United States Patent [19]

Bolich, Jr. et al.

[11] Patent Number: 5,100,658

[45] Date of Patent: Mar. 31, 1992

[54] VEHICLE SYSTEMS FOR USE IN COSMETIC COMPOSITIONS

[75] Inventors: Raymond E. Bolich, Jr., Maineville; Michael J. Norton, Cincinnati; Glen D. Russell, Loveland, all of Ohio

[73] Assignee: The Procter & Gamble Company, Cincinnati, Ohio

[21] Appl. No.: 551,118

[22] Filed: Jul. 16, 1990

Related U.S. Application Data

[63] Continuation-in-part of Ser. No. 390,328, Aug. 7, 1989, abandoned.

[51] Int. Cl.$^5$ ............ A61K 7/08; A61K 7/13; A61K 7/48
[52] U.S. Cl. ...................... 424/70; 424/71; 8/405; 514/781
[58] Field of Search ............ 424/70, 78, DIG. 1, 424/DIG. 71; 514/781; 8/405

[56] References Cited

U.S. PATENT DOCUMENTS

| | | | |
|---|---|---|---|
| 3,395,041 | 7/1968 | Hsiung | 132/7 |
| 3,579,632 | 5/1971 | Sonnen | 424/70 |
| 3,580,853 | 5/1971 | Parran | 252/152 |
| 3,723,325 | 3/1973 | Parran | 252/106 |
| 4,228,277 | 10/1980 | Landoll | 536/90 |
| 4,243,802 | 1/1981 | Landoll | 536/91 |
| 4,298,728 | 11/1981 | Majewicz et al. | 536/96 |
| 4,299,817 | 11/1981 | Hannan, III et al. | 424/70 |
| 4,331,167 | 5/1982 | Wajaroff | 132/7 |
| 4,336,246 | 6/1982 | Leon-Pekarek | 424/70 |
| 4,352,916 | 10/1982 | Landoll | 526/200 |
| 4,374,825 | 2/1983 | Bolich, Jr. et al. | 424/70 |
| 4,415,701 | 11/1983 | Bauer | 524/612 |
| 4,421,740 | 12/1983 | Burton | 424/70 |
| 4,426,485 | 1/1984 | Hoy et al. | 524/591 |
| 4,435,217 | 3/1984 | House | 106/171 |
| 4,458,068 | 7/1984 | Warner et al. | 536/91 |
| 4,459,285 | 7/1984 | Grollier et al. | 424/74 |
| 4,465,517 | 8/1984 | Shields | 106/35 |
| 4,485,089 | 11/1984 | Leipold | 424/49 |
| 4,496,708 | 1/1985 | Dehm et al. | 528/76 |
| 4,501,617 | 2/1985 | Desmarais | 106/93 |
| 4,523,010 | 6/1985 | Lukach et al. | 536/91 |
| 4,529,523 | 7/1985 | Landoll | 252/8.55 D |
| 4,557,928 | 12/1985 | Glover | 424/70 |
| 4,581,230 | 4/1986 | Grollier et al. | 424/74 |
| 4,584,189 | 4/1986 | Leipold | 424/54 |
| 4,610,874 | 9/1986 | Matravers | 424/70 |
| 4,683,004 | 7/1987 | Goddard | 106/170 |
| 4,684,704 | 8/1987 | Craig | 526/200 |
| 4,707,189 | 11/1987 | Nickol | 106/176 |
| 4,725,433 | 2/1988 | Matravers | 424/70 |
| 4,726,944 | 2/1988 | Osipow et al. | 424/70 |
| 4,788,006 | 11/1988 | Bolich, Jr. et al. | 252/550 |
| 4,826,970 | 5/1989 | Reid et al. | 536/66 |
| 4,883,536 | 11/1989 | Burdick | 106/194 |
| 4,894,224 | 1/1990 | Kuwata et al. | 424/78 |
| 4,902,499 | 2/1990 | Bolich, Jr. et al. | 424/70 |

FOREIGN PATENT DOCUMENTS 0170927 2/1986 European Pat. Off.
54-043210 4/1979 Japan.
84-007758 2/1984 Japan.
85-023151 6/1985 Japan.
85-026401 6/1985 Japan.
61-053211 3/1986 Japan.
86-023764 6/1986 Japan.
61-151105 7/1986 Japan.
61-186306 8/1986 Japan.
87-195963 8/1987 Japan.
62-294606 12/1987 Japan.
2185269A 7/1987 United Kingdom.

OTHER PUBLICATIONS

Amer. Chem. Soc., Spring Mtg. 1987; Denver, Co.; Symposium notes, Div. of Polymeric Mat'ls: Science and Engineering, vol. 56, presentation of a Sau 194th Nat'l Mtg. of ACS, New Orleans, La., 8/30-9/4/87;
Glass, J. E., et., Advances in Chem. Series, 0065-2393; 223, pp. 344-364.
Gelman, R. A., International Dissolving Pulp Conference, Tappi, Feb. 1987, pp. 159-165.
Steiner, C. A., Polymer Prepr. (Am. Chem. Soc., Div. Polym. Chem.) 1985, 26(1), pp. 224-225.
Chem. Abs. 130:27060b, Hercules Inc. Research Disclosure-252002, 1985 Publication.
Hercules Inc. Research Disclosure-252021.
Hercules Inc. Development Data-15 Publication.
Hercules Inc. Development Data-16 Publication.
Hercules Inc. Development Data-32 Publication.
Hercules Inc. Research Publication dated Nov. 2, 1984, entitled "Update WSP D-340 Performance in Surfactant Systems".

Primary Examiner—Thurman K. Pace
Assistant Examiner—Susan S. Rucker
Attorney, Agent, or Firm—Leonard W. Lewis; Steven J. Goldstein

[57] ABSTRACT

Disclosed is a unique vehicle system which provides a desirable rheology to products formulated therewith, enhanced dispersion of actives therein, and improved deposition of actives therefrom. This vehicle system comprises a primary thickening agent which is a nonionic long-chain alkylated water-soluble polymer, and a secondary thickening agent which is a water-soluble polymer having a molecular weight greater than about 20,000, preferably a natural polysaccharide, dispersed in a compatible solvent. Optionally, a rheological aid, which is a chelating agent, may be included in the vehicle system. Also, optionally, a distributing aid, which is a water-soluble polymer of either high molecular weight or strong ionic character may be included in the vehicle system. These vehicle systems are useful in cosmetic compositions which are used to deliver an active component to the skin or hair. The vehicle systems are particularly useful in hair care compositions, especially rinse-off hair conditioning compositions, because they effectively deliver the hair conditioning component to the hair without depositing a substantial amount of the vehicle material onto the hair.

44 Claims, No Drawings

VEHICLE SYSTEMS FOR USE IN COSMETIC COMPOSITIONS

TECHNICAL FIELD

This application is a continuation-in-part of U.S. application Ser. No. 390,328, Bolich et al., filed Aug. 7, 1989 now abandoned.

The present invention relates to novel vehicle systems, and cosmetic compositions formulated therewith, based on particular nonionic long chain alkylated water-soluble polymer derivatives and water-soluble polymers having a molecular weight greater than about 20,000, dispersed in a compatible solvent. A particularly useful application of the present invention is in hair care compositions, especially rinse-off hair conditioning compositions.

BACKGROUND OF THE INVENTION

Typical hair conditioning products have a particular thick rheology that is desirable for such products. These products are based on the combination of a surfactant, which is generally a quaternary ammonium compound, and a fatty alcohol. This combination results in a gel-network structure which provides the composition with a thick rheology. However, while such compositions deliver conditioning benefits to the hair, such compositions also deposit on hair making hair look and feel dirty.

Alternative thickening systems have been used in hair care compositions, but none have been found to date which provide this same desirable rheology. Through hair care products thickened with polymer thickeners can be made to have a thick rheology, these products generally are characterized by an undesirable "slimy" feel and do not hold their poured shape.

Nonionic water-soluble cellulose ethers are employed in a variety of applications, including hair care compositions. Widely used, commercially-available nonionic cellulose ethers include methyl cellulose, hydroxy propyl methyl cellulose, hydroxyethyl cellulose, hydroxypropyl cellulose and ethyl hydroxyethyl cellulose.

Better thickening efficiency is realized with higher molecular weight cellulose ethers. However, production of such materials is difficult and expensive. Though crosslinking of these polymers is an alternative means to achieve high viscosity solutions, good crosslinking techniques are not known. Of course, high concentrations of polymers will also provide high viscosity but such an approach is inefficient and impractical, particularly due to the high expense involved. Furthermore, use of highly crosslinked polymers or high levels of polymeric thickeners may result in a vehicle system that is too elastic for the present uses.

Alternative water-soluble polymeric thickeners sometimes used to thicken hair care compositions are natural polysaccharides such as guar gum, xanthan, gum and locust bean gum.

The number of references teach the use of nonionic cellulose ethers and water-soluble gums for thickening hair care compositions. See for example, U.S. Pat. No. 4,557,928, Glover, issued Dec. 10, 1985, teaching a hair conditioner comprising a suspension system which consists of one of glucan gum, guar gum, and hydroxyethylcellulose; and U.S. Pat. No. 4,581,230, Grollier et al., issued Apr. 8, 1986, which teaches cosmetic compositions for treating hair which comprise as thickening agents hydroxyethylcellulose, or water-soluble vegetable thickening agents, such as guar gum. Japanese Patent Publication 61-053211, published Mar. 7, 1986, discloses a hair colorant containing an aromatic alcohol, xanthan gum, and hydroxyethylcellulose.

Certain cellulose ethers have been disclosed in U.S. Pat. No. 4,228,277, Landoll, issued Oct. 14, 1980, which are relatively low molecular weight but which are capable of producing highly viscous aqueous solutions in practical concentrations. These materials are nonionic cellulose ethers having a sufficient degree of nonionic substitution selected from the group consisting of methyl, hydroxyethyl, and hydroxypropyl to cause them to be water-soluble and which are further substituted with a hydrocarbon radical having from about 10 to 24 carbon atoms in an amount between about 0.2 weight percent and the amount which renders said cellulose ether less than 1%, by weight, soluble in water. The cellulose ether to me modified is preferably one of low to medium molecular weight; i.e., less than about 800,000 and preferably between about 20,000 and 700,000 (about 75 to 2500 D.P.).

These modified cellulose ethers have been disclosed for use in a variety of composition types. Landoll ('277) teaches the use of these materials in shampoo formulations. Hercules trade literature teaches the use of these materials in shampoos, liquid soaps, and lotions. U.S. Pat. No. 4,683,004, Goddard, issued July 28, 1987, discloses the use of their materials in mousse composition for the hair. U.S. Pat. No. 4,485,089, Leipold, issued Nov. 27, 1984, teaches dentrifice compositions containing these materials.

These materials have now been found to provide a rheology very much like the desirable gel-network structure of typical hair conditioners (without the slimy feel associated with most polymeric thickeners), when they are combined with additional water-soluble polymeric thickeners, having a molecular weight greater than about 20,000, such as natural thickening gums, at certain levels.

Hence, it is an object of the present invention to provide a vehicle system for hair care and other cosmetic compositions which provides a gel-network-like structure to the composition but which is not based on a typical quaternary ammonium compound/fatty alcohol gel-network thickening system.

It is also an object of the present invention to provide a vehicle system for hair care and other cosmetic compositions which allows for dispersion of a wide variety of active hair or skin care components therein.

It is also an object of the present invention to provide a vehicle system for hair care or other cosmetic compositions which will maximize deposition of the active hair or skin care component contained therein onto hair or skin while minimizing the deposition of the vehicle system components.

These and other objects will become readily apparent from the detailed description which follows.

SUMMARY OF THE INVENTION

The present invention relates to unique vehicle systems for use in cosmetic compositions which are polymer-based but which provide a rheology to the cosmetic compositions which mimics gel-network systems. These vehicle systems are based on a two-component thickening system. More specifically, the cosmetic compositions of the present invention comprise:

(a) from about 80% to about 100%, preferably from about 80% to about 99.9%, of a vehicle system which comprises:
   (A) from about 0.3% to about 5.0% by weight of the cosmetic composition of a hydrophobically modified nonionic water-soluble polymer which comprises a water-soluble polymer backbone and hydrophobic groups selected from the group consisting of $C_8$-$C_{22}$ alkyl, aryl alkyl, alkylaryl groups and mixtures thereof; wherein the ratio of the hydrophilic portion to the hydrophobic portion of the polymer is from about 10:1 to about 1000:1; preferably the hydrophobically modified nonionic water-soluble polymer comprises a nonionic cellulose ether having a sufficient degree of nonionic substitution selected from the class consisting of methyl, hydroxyethyl and hydroxypropyl to cause it to be water-soluble and being further substituted with a long chain alkyl radical having 10 to 22 carbon atoms in an amount which renders said cellulose ether less than 1% by weight soluble in water;
   (B) from about 0.3% to about 5.0% by weight of the cosmetic composition of a water-soluble polymeric thickener having a molecular weight greater than about 20,000; and
   (C) from about 65% to about 99% by weight of the cosmetic composition, of a compatible solvent; and
(b) from 0% to about 20%, preferably from about 0.1% to about 20% of an active cosmetic component;
wherein compositions comprising said vehicle system comprise no more than about 1.0%, preferably no more than about 0.5%, of water-soluble surfactant materials.

The vehicle system provides a rheology to the cosmetic compositions formulated therewith, that is preferably characterized by a shear stress of from 0 to about 50 pascal over a shear rate range of from about 0.04 $sec^{-1}$ to about 25 $sec^{-1}$. These vehicle systems are particularly useful in hair care compositions especially rinse-off hair conditioners. Most preferably the hair care compositions formulated with these unique vehicle systems comprise no more than about 1% of fatty alcohol materials.

DETAILED DESCRIPTION OF THE INVENTION

The essential as well as optional components of the present compositions are described below.

Primary Thickener

The vehicle systems of the present invention contain, as an essential component, a primary thickening material. The primary thickening material is a hydrophobically modified nonionic water-soluble polymer. By "hydrophobically modified nonionic water-soluble polymer" is meant a nonionic water-soluble polymer which has been modified by the substitution with a sufficient amount of hydrophobic groups to make the polymer less soluble in water. Hence, the polymer backbone of the primary thickener can be essentially any water-soluble polymer. The hydrophobic groups can be $C_8$ to $C_{22}$ alkyl, aryl alkyl, alkyl aryl groups and mixtures thereof. The degree of hydrophobic substitution on the polymer backbone should be from about 0.10% to about 1.0%, depending on the particular polymer backbone. More generally, the ratio of hydrophilic portion to hydrophobic portion of the polymer is from about 10:1 to about 1000:1.

A number of existing patents disclose nonionic polymer materials which meet the above requirements and which are useful in the present invention. U.S. Pat. No. 4,496,708, Dehm et al., issued Jan. 29, 1985, teaches water-soluble polyurethanes having hydrophilic polyether backbones and pendant monovalent hydrophobic groups to result in a hydrophilic/lipophilic balance of between about 14 and about 19.5. U.S. Pat. No. 4,426,485, Hoy et al., issued Jan. 17, 1984, discloses a water-soluble thermoplastic organic polymer having segments of bunched monovalent hydrophobic groups. U.S. Pat. No. 4,415,701, Bauer, issued Nov. 15, 1983, discloses copolymer containing a monoepoxide and a dioxolane.

The most preferred primary thickener materials for use in the present invention are disclosed in U.S. Pat. No. 4,228,277, Landoll, issued Oct. 14, 1980, which is incorporated herein by reference. The materials disclosed therein are thickeners comprising a nonionic long chain alkylated cellulose ether.

The cellulose ethers have a sufficient degree of nonionic substitution selected from the group consisting of methyl, hydroxyethyl and hydroxypropyl to cause them to be water-soluble. The cellulose ethers are further substituted with a hydrocarbon radical having about 10 to 22 carbon atoms in an amount between about 0.2 weight percent and the amount which renders said cellulose ether less than 1%, by weight, soluble in water. The cellulose ether to be modified is preferably one of low to medium molecular weight, i.e., less than about 800,000 and preferably between about 20,000 and 700,000 (about 75 to 2500 D.P.).

The Landoll ('277) patent teaches that any nonionic water-soluble cellulose ether can be employed as the cellulose ether substrate. Thus, e.g., hydroxethyl cellulose, hydroxypropyl cellulose, methyl cellulose, hydroxypropyl methyl cellulose, ethyl hydroxyethyl cellulose, and methyl hydroxyethyl cellulose can all be modified. The amount of nonionic substituent such as methyl, hydroxyethyl or hydroxypropyl is taught not to be critical so long as there is an amount sufficient to assure that the ether is water-soluble.

The preferred cellulose ether substrate is hydroxyethyl cellulose (HEC) of about 50,000 to 700,000 molecular weight. Hydroxyethyl cellulose of this molecular weight level is the most hydrophilic of the materials contemplated. It can thus be modified to a greater extent than can other water-soluble cellulose ether substrates before insolubility is achieved. Accordingly, control of the modification process and control of the properties of the modified product can be more precise with this substrate. Hydrophilicity of the most commonly used nonionic cellulose ethers varies in the general direction: hydroxyethyl→hydroxypropyl→hydroxypropylmethyl→methyl.

The long chain alkyl modifier can be attached to the cellulose ether substrate via an ether, ester or urethane linkage. The ether linkage is preferred.

Although the materials taught in Landoll are referred to as being "long chain alkyl group modified", it will be recognized that except in the case where modification is effected with an alkyl halide, the modifier is not a simple long chain alkyl group. The group is actually an alphahydroxyalkyl radical in the case of an epoxide, a urethane radical in the case of anisocyanate, or an acyl radical in the case of an acid or acyl chloride. Nonetheless, the terminology "long chain alkyl group" is used since the size and effect of the hydrocarbon portion of the modifying molecule completely obscure any noticeable effect from the connecting group. Properties are not significantly different from those of the product modified with the simple long chain alkyl group.

Methods for making these modified cellulose ethers are taught in Landoll ('277) at column 2, lines 36-65.

These materials have been found to be particularly desirable for use in the vehicle systems of the cosmetic compositions of the present invention. The materials are broadly compatible with anionic and cationic materials, they are able to stabilize suspensions of dispersed phases and, when used with the additional components in the vehicle systems of the present invention, they produce rheologically thick products which lack the slimy feel characteristics of most polymeric thickeners.

One commercially available material which meets these requirements is NATROSOL PLUS Grade 330, a hydrophobically modified hydroxyethylcellulose available from Aqualon Company, Wilmington, Del. This material has a $C_{16}$ alkyl substitution of about 0.4% to about 0.8% by weight. The hydroxyethyl molar substitution for this material is from about 3.0 to about 3.7. The average molecular weight of the water-soluble cellulose prior to modification is approximately 300,000.

Another material of this type is sold under the trade name NATROSOL PLUS CS Grade D-67, also by Aqualon Company, Wilmington, Del. This material has a $C_{16}$ alkyl substitution of from about 0.50% to about 0.95%, by weight. The hydroxyethyl molar substitution for this material is from about 2.3 to about 3.3, and may be as high as about 3.7. The average molecular weight for the water soluble cellulose prior to modification is approximately 700,000.

The primary thickener component is present in the cosmetic compositions of the present invention at from about 0.3% to about 5.0%, preferably from about 0.4% to about 3.0%.

It is important that the primary thickener be well-hydrated and dispersed in the compositions of the present invention.

Additional Thickener

The present vehicle systems further comprises, as a second essential component, an additional thickening component, which comprises a water-soluble polymeric material, having a molecular weight greater than about 20,000. By "water-soluble polymer" is meant that the material will form substantially a clear solution in water at a 1% concentration at 25° C. and the material will increase the viscosity of the water. Examples of water-soluble polymers which are desirably used as the additional thickening component in the present vehicle systems, include hydroxyethylcellulose, hydroxypropyl cellulose, hydroxypropyl methylcellulose, polyethylene glycol, polyacrylamide, polyacrylic acid, polyvinyl alcohol, polyvinyl pyrrolidone K-120, dextrans, for example Dextran purified crude Grade 2P, available from D&O Chemicals, carboxymethylcellulose, plant exudates such as acacia, ghatti, and tragacanth, seaweed extracts such as sodium alginate, propylene glycol alginate, sodium carrageenan, and Ucare JR-polymer (a cationic modified hydroxyethyl cellulose available from Union Carbide). Preferred ad the additional thickener for the present vehicle systems are natural polysaccharide materials. Examples of such materials are guar gum, locust bean gum, and xanthan gum. Also preferred as the additional thickener in the present compositions is hydroxyethylcellulose having a molecular weight of about 700,000. It is important that these polymer materials not contain cellulose as this may interfere with obtaining optimum product viscosities.

The additional thickening component is present in the cosmetic compositions of the present invention at from about 0.3% to about 5.0%, preferably from about 0.4% to about 3.0%.

It is important that these additional polymer materials be well hydrated and dispersed in the present composition.

Solvent

A third essential component in the vehicle system of the present invention is a solvent which is compatible with the other components in the present compositions. Generally the solvent will comprise water, or a water-lower alkanol mixture. The solvent is present in the compositions of the present invention at a level of from about 65% to about 99% by weight of the cosmetic composition.

The other vehicle components are dispersed or mixed in the solvent to provide an optimum thick rheology to cosmetic compositions formulated therewith which mimics the gel-network rheology of typical hair conditioning compositions. This rheology is characterized by a shear stress of from 0 to 50 pascal, over a shear rate range of 0.04 $sec^{-1}$ to 25 $sec^{-1}$. The rheology is measured using a Bohlin Rheometer VOR with the following cone and plate set-up: cone has a 2.5 degree angle, plate is 30 mm in diameter, the gap between the truncated cone and plate is set at 70 $\mu$m, and the torque bar used is 20.148 g-cm. The sample amount is 0.35 ml and the sample is syringed onto the center of the plate. The system used is as follows: there is no initial delay time, the strain delay time is 25 sec, the integration time is 5 sec, the sensitivity is set at 1 X, the shear sweep is up, the shear range is from about 0.0405 $sec^{-1}$ to 25.53 $sec^{-1}$ (shear No. =11 to 39), and the temperature is maintained constant between series at ambient temperature (20° C. to 25° C.).

Rheological Aid

The vehicle systems of the present invention preferably also contain a material which provides additional rheological benefits to the cosmetic compositions formulated therewith. These materials are chelating agents. In general, such materials include monodentate and multidentate agents. Specific examples of useful chelating agents include ethylenediaminetetraacetic acid (EDTA) and salts thereof, a nitrilotriacetic acid (NTA) and salts thereof, hydroxy ethyl ethylenediamine triacetic acid (HEEDTA) and salts thereof, diethylene triamine pentaacetic acid (DTPA) and salts thereof, diethanolglycine (DEG) and salts thereof, ethanoldiglycine (EDG) and salts thereof, citric acid and salts thereof, phosphoric acid and salts thereof. The most preferred of these is EDTA.

The chelating agents tend to make the vehicle systems of the present invention smoother and less gelatinous in consistency. If a chelating agent is present as a rheological aid in the cosmetic compositions of the present invention it is present at a level of from about 0.05% to about 1.0%, preferably from about 0.05% to about 0.3%, of the composition.

Distributing Aid

An additional optional component in the vehicle systems of the present invention is a material which acts as a distributing aid for the composition. Such a material helps to distribute the cosmetic composition onto the hair or skin avoiding localized deposition of the active component onto the hair or skin. Without such a component in the composition, some active components in the composition would not be deposited and spread out as evenly, and hence, would not be quite as effective.

Distributing aid materials useful in the present invention are actually a subclass of the class of materials used as the additional thickener in the present invention. The subclass is defined as follows: water-soluble polymer materials having high molecular weight, i.e., greater than 1,000,000; and/or strong ionic character. By strong ionic character is meant that the material conducts electricity at greater than 30 millivolts. This can be measured by evaluating conductance of a 1% solution of polymer in DRO (double reverse osmosis) water preserved with 0.03% Kathon CG (a preservative available from Rohm & Haas) using a calibrated Corning 130 pH meter. The probes used are as follows. The reference electrode is an Orion Model 9001 single junction. The pH electrode is an Orion Model 9161, silver-silver chloride. The probes are set ⅜ of an inch apart. The pH meter is set to millivolt readings. The absolute measurement is recorded after 4 minutes immersion.

Examples of water-soluble polymer materials which meet these requirements and hence, can act as distributing aids in the present compositions, include xanthan gum; Dextran purified crude Grade 2P available from D&O Chemicals; carboxymethyl cellulose, for example, CMC's 4H1F, 4M6F, 7HF, 7M8SF, 7LF, 9H4F, 9M8, 12M8P, 16M31 (all available from Aqualon); plant exudates such as acacia, ghatti and tragacanth; seaweed extracts such as sodium alginate, propylene glycol alginate, and sodium carrageenan; high molecular weight hydroxyethylcelluloses such as Natrosol 250H and Natrosol 250HR (available from Aqualon); and pectin.

Because the class of materials which may act as distributing aids in the present invention is a subset of the class of materials which act as additional thickeners in the present invention, the materials in this subclass may be used to provide both benefits to the composition. For example, xantham gum is a water-soluble natural polysaccharide material which additionally has a high molecular weight. Hence, this material could be used to itself to provide both additional thickening benefits and distributing benefits. However, it may be necessary to use such materials at slightly higher levels to provide both benefits.

It is also possible to use two separate materials as the additional thickener and distributing aid of the present invention. This would be done when the additional thickener chosen was not a high molecular weight material or of strong ionic character. Locust bean gum is such a material. A distributing aid such as xanthan gum could be used with locust bean gum to provide the additional distributing benefits.

If the distributing aid is present in the cosmetic compositions of the present invention, it should be present at a level of from about 0.02% to about 2.5%, preferably from about 0.05% to about 1.0% of the cosmetic composition. If the distributing aid is bifunctional, i.e., acting as both the additional thickener and the distributing aid it should be present at a level of from about 0.2% to about 5.0% of the cosmetic composition.

A distributing aid is particularly useful in hair care compositions of the present invention, especially rinse-off hair conditioners. The distributing aid helps to spread some hair conditioning components evenly over the hair.

The present vehicle systems and cosmetic compositions formulated therewith must be substantially free of water-soluble surfactants. These materials are not compatible with the vehicle systems of the present composition. By "substantially free of water-soluble surfactants" is meant that the compositions comprise less than an amount of such surfactants that will destroy the present unique desirable rheology that is the object of the present invention. Generally, this will mean that the present compositions comprise no more than about 1%, preferably no more than about 0.5%, of such materials. Examples of specific water-soluble surfactant materials that can be particularly harmful to the present vehicle system are alkyl sulfates and ethoxylated alkyl sulfates, such as ammonium lauryl sulfate; amphoteric surfactants which are derivatives of aliphatic secondary and tertiary amines; nonionic surfactants produced by the condensation of alkylene oxide groups with an organic hydrophilic compound, such as laureth-23 (sold under the trademark Brij 35 by ICI Americas); and high alkyl betaines, sulfo betaines. Such materials are commonly used in hair shampoo compositions.

The present vehicle systems and cosmetic compositions formulated therewith are also preferably substantially free of fatty alcohol materials such as stearyl alcohol, cetyl alcohol, myristyl alcohol, benehyl alcohol, lauryl alcohol and oleyl alcohol. By "substantially free of fatty alcohol materials" is meant that the compositions of the present invention comprise no more than about 1% of these materials. These materials are commonly used in vehicle systems for hair conditioner products. However, these materials are undesirable because they tend to deposit on the hair and leave the hair feeling dirty after use. These materials are not required and are not desirable in the present vehicle systems, as they are thickened with alternative materials which do not deposit on hair.

The present vehicle systems can be used in essentially any cosmetic products having a thick gel-network type rheology and which are used to deliver some active component onto the hair or skin. Such compositions would include skin moisturizing lotions, sunscreen compositions, and skin cleansing compositions. However, cosmetic compositions most desirably used with the present vehicle systems are hair care products, especially rinse-off hair care products where some active hair care component is to be deposited onto the hair but the vehicle carrying that component is desirably rinsed off of the hair with little or no deposition of the vehicle material onto the hair.

Generally, the present vehicle systems will not be useful in typical shampoo compositions since these compositions contain high levels of water-soluble surfactants, which, as discussed supra, are incompatible with the present vehicle systems. However, the present vehicle systems are useful in typical hair coloring compositions, hair tonic or gel compositions, hair mousse compositions, and especially hair conditioning compositions.

Active Cosmetic Component

The cosmetic compositions of the present invention generally will comprise some active component which provides some benefit to the hair or skin. Such materials may include moisturizing agents, suncreen agents, cleaning agents (that are compatible with the present vehicle systems), and especially hair conditioning agents, hair styling agents, antidandruff agents, hair growth promoters, hair dyes and pigments, or perfumes.

A wide variety of conventional sunscreening agents are suitable for use in the cosmetic compositions of the present invention. Segarin, et al., at Chapter VIII, pages 189 et seq., of *Cosmetics Science and Technology*, disclose numerous suitable agents. Specific suitable sunscreening agents include, for example: p-aminobenzoic acid, its salts and its derivatives; anthranilates; salicylates; cinnamic acid derivatives; dihydroxycinnamic acid derivatives; trihydroxycinnamic acid derivatives; hydrocarbons; dicenzalacetone and benzalacetophenone; naphtholsulfonates; dihydroxy-naphtholic acid and its salts; coumarin derivatives; diazoles; quinine salts; quinoline derivatives; hydroxy- and methoxy-substituted benzophenones; uric and vilouric acids; tannic acid and its derivatives; hydroquinone; and benzophenones.

Of these, 2-ethylhexyl p-methoxycinnamate, 4,4'-t-butyl methoxydibenzolymethane, 2-hydroxy-4-methoxybenzophenone, octyldimethyl p-aminobenzoic acid, digalloyltrioleate, 2,2-dihydroxy-4-methoxybenzophenone, ethyl 4-[bis(hydroxypropyl)]-aminobenzoate, 2-ethylhexyl-2-cyano-3,3-diphenylacrylate, 2-ethylhexylsalicylate, glyceryl p-aminobenzoate, 3,3,5-tri-methylcyclohexylsalicylate, methylanthranilate, p-dimethylaminobenzoic acid or aminobenzoate, 2-ethylhexyl p-dimethylaminozoate, 2-phenylbenzimidazole-5-sulfonic acid 2-(p-eimethylaminophenyl)-5-sulfonicbenzoxazoic acid, and mixtures of these compounds, are particularly useful.

Examples of antidandruff aids suitable for use with the vehicle systems of the present invention include zinc pyrithione, sulphur-containing compounds, and selenium sulfide. One example of a hair growth promoter suitable for use with the vehicle systems of the present invention is Minoxidil (5-amino-1,2-dihydro-1-hydroxy-2-imino-4-piperidinopyrimidine) available from Upjohn. Hair oxidizing (bleaching) agents, such as hydrogen peroxide, perborate, and persulfate salts, and hair reducing agents such as thioglycolates may also be used.

Examples of hair conditioning materials suitable for use in the vehicle systems of the present invention are volatile liquid hydrocarbon or silicone agents.

These materials preferably have a boiling point in the range of about 99° C. to about 260° C. and have a solubility in water of less than about 0.1%. The hydrocarbons may be either straight or branched chain and may contain from about 10 to about 16, preferably from about 12 to about 16, carbon atoms. Examples of suitable hydrocarbons are decane, dodecane, tetradecane, tridecane and mixtures thereof.

The volatile silicones useful as the active hair treating component in the compositions of the present invention may be either a cyclic or a linear polydimethylsiloxane. The number of silicon atoms in the cyclic silicones is preferably from about 3 to about 7, more preferably 4 or 5.

The general formula for such silicones is

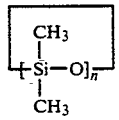

wherein n=3-7. The linear polydimethylsiloxanes have from about 3 to 9 silicon atoms and have the general formula:

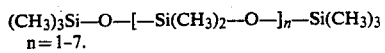

n=1-7.

Silicones of the above type, both cyclic and linear, are available from Down Corning Corporation, Dow Corning 344, 345 and 200 fluids; Union Carbide, Silicon 7202 and Silicone 7158; and Stauffer Chemical, SWS-03314.

The linear volatile silicones generally have viscosities of less than about 5 centipoise at 25° C. while the cyclic materials have viscosities less than about 10 centipoise. "Volatile" means that the material has a measurable vapor pressure. A description of volatile silicones is found in Todd and Byers, "Voltatile Silicone Fluids for Cosmetics", Cosmetics and Toiletries, Vol. 91, January 1976, pp. 27-32, incorporated herein by reference.

The volatile agent may be present in the compositions of this invention at a level of from about 1% to about 20%, preferably from about 2% to about 15%. The volatile silicones are the preferred volatile agents.

Nonvolatile silicon fluids are also useful as the active hair care component in the compositions of the present invention. Examples of such materials include polydimethylsiloxane gums, aminosilicones and phenylsilicones. More specifically, materials such as polyalkyl or polyaryl siloxanes with the following structure:

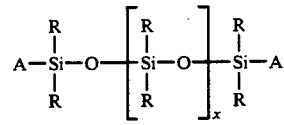

wherein R is alkyl or aryl, and x is an integer from about 7 to about 8,000 may be used. A represents groups which block the ends of the silicone chains.

The alkyl or aryl groups substituted on the siloxane chain (R) or at the ends of the siloxane chains (A) may have any structure as long as the resulting silicones remain fluid at room temperature, are hydrophobic, are neither irritating, toxic nor otherwise harmful when applied to the hair, are compatible with the other components of the composition, are chemically stable under normal use and storage conditions, and are capable of being deposited on and of conditioning hair.

Suitable A groups include methyl, methoxy, ethoxy, propoxy, and aryloxy. The two R groups on the silicone atom may represent the same group or different groups. Preferably, the two R groups represent the same group. Suitable R groups include methyl, ethyl, propyl, phenyl, methylphenyl and phenylmethyl. The preferred silicones are polydimethyl siloxane, polydiethylsiloxane, and polymethylphenylsiloxane, polydimethylsiloxane is especially preferred.

Suitable methods for preparing these silicone materials are disclosed in U.S. Pat. Nos. 2,826,551 and 3,964,500 and references cited therein. Silicones useful in the present invention are also commercially available. Suitable examples include Viscasil, a trademark of the General Electric Company and silicones offered by Dow Corning Corporation and by SWS Silicones, a division of Stauffer Chemical Company.

Other useful silicone materials include materials of the formula:

$$\text{HO} \left[ \begin{array}{c} CH_3 \\ | \\ Si-O \\ | \\ CH_3 \end{array} \right]_x \left[ \begin{array}{c} OH \\ | \\ SiO \\ | \\ (CH_2)_3 \\ | \\ NH \\ | \\ (CH_2)_2 \\ | \\ NH_2 \end{array} \right]_y \text{H} \quad (I)$$

in which x and y are integers which depend on the molecular weight, the average molecular weight being approximately between 5,000 and 10,000. This polymer is also known as "amodimethicone".

Other silicone cationic polymers which can be used in the present composition correspond to the formula:

$(R_1)_a G_{3-1} - Si - (-OSiG_2)_n - OSiG_b(R_1)_{2-b})_m - O - SiG_{3-a}(R_1)_a$ in which G is chosen from the group consisting of hydrogen, phenyl, OH, $C_1$-$C_8$ alkyl and preferably methyl; a denotes 0 or an integer from 1 to 3, and preferably equals 0;

b denotes 0 or 1 and preferably equals 1; the sum n+m is a number from 1 to 2,000 and preferably from 50 to 150, n being able to denote a number from 0 to 1,999 and preferably from 49 to 149 and m being able to denote an integer from 1 to 2,000 and preferably from 1 to 10;

$R_1$ is a monovalent radical of formula $C_1H_{2q}L$ in which q is an integer from 2 to 8 and L is chosen from the groups $-N(R_2)CH_2-CH_2-N(R_2)_2$
$-N(R_2)_2$ $-\overset{+}{N}(R_2)_3 A^-$ $-\overset{+}{N}(R_2)CH_2-CH_2-\overset{+}{N}R_2H_2 A^-$ in which $R_2$ is chosen from the group consisting of hydrogen, phenyl, benzyl, a saturated hydrocarbon radical, preferably an alkyl radical containing from 1 to 20 carbon atoms, and $A^-$ denotes a halide ion.

These compounds are described in greater detail in European Patent Application EP 95,238. An especially preferred polymer corresponding to this formula is the polymer known as "trimethylsilylamodimethicone" of formula:

$$(CH_3)_3-Si \left[ \begin{array}{c} CH_3 \\ | \\ O-Si \\ | \\ CH_3 \end{array} \right]_n \left[ \begin{array}{c} CH_3 \\ | \\ O-Si \\ | \\ (CH_2)_3 \\ | \\ NH \\ | \\ (CH_2)_2 \\ | \\ NH_2 \end{array} \right]_m OSi(CH_3)_3 \quad (II)$$

Compositions of the present invention may comprise up to about 1.0% of a trimethylsilyl amodimethicone silicone conditioning material.

Other silicone cationic polymers which can be used in the present compositions correspond to the formula:

$$(R_3)_3-Si-O \left[ \begin{array}{c} Si-O \\ | \\ R_3 \end{array} \right]_r \left[ \begin{array}{c} R_3 \\ | \\ Si-O \\ | \\ R_3 \end{array} \right]_s Si-(R_3)_3 \quad (III)$$

$$R_4-CH_2-CHOH-CH_2-\overset{+}{N}(R_3)_3 Q^-$$

in which $R_3$ denotes a monovalent hydrocarbon radical having from 1 to 18 carbon atoms, and more especially an alkyl or alkenyl radical such as methyl;

$R_4$ denotes a hydrocarbon radical such as, preferably a $C_1$-$C_{18}$ alkylene radical or a $C_1$-$C_{18}$, and preferably $C_1$-$C_8$, alkyleneoxy radical;

$Q^-$ is a halide ion, preferably chloride;

r denotes an average statistical value from 2 to 20, preferably from 2 to 8;

s denotes an average statistical value from 20 to 200, and preferably from 20 to 50.

These compounds are described in greater detail in U.S. Pat. No. 4,185,017.

A polymer of this class which is especially preferred is that sold by UNION CARBIDE under the name "UCAR SILICONE ALE 56".

Silicone conditioning agents are used in the present compositions at levels of from about 0.1% to about 18%, preferably from about 0.5% to about 15%.

Preferred silicone conditioning agents for use in the present compositions comprise combinations of volatile silicone fluids having viscosities of less than about 10 centipoise, and from about 0.015% to about 9.0%, preferably from about 0.5% to about 2.0%, of silicone gums having viscosities of greater than about 1,000,000 centipoise, at ratios of volatile fluid to gum of from about 90:10 to about 10:90, preferably from about 85:15 to about 50:50.

Alternative preferable non-volatile silicone materials for use in the present invention comprise non-volatile silicone fluids having viscosities of less than about 100,000 cP (centipoise), and from about 0.015% to about 9.0%, preferably from about 0.5% to about 2.0%, of silicone gums having viscosities greater than about 1,000,000 cP, especially polydimethylsiloxane gums and polyphenylmethylsiloxane gums, at ratios of non-volatile fluid to gum of from about 70:30 to about 30:70, preferably from about 60:40 to about 40:60.

Other preferred active hair care materials for use with the vehicle systems of the present invention are silicone polymer materials which provide both style retention and conditioning benefits to the hair. Although silicone fluids are useful in the present compositions, preferred silicone polymers are rigid silicon polymers. Such materials are described in U.S. Pat. No. 4,902,499, Bolich et al., issued Feb. 20, 1990, and U.S. Pat. No. 4,906,459, Bolich et al., issued Mar. 6, 1990.

Some examples of such materials include, but are not limited to, filler reinforced polydimethyl siloxane gums including those having end groups such as hydroxyl; cross linked siloxanes, such as organic substituted silicone elastomers; organic substituted siloxane gums, including those having end groups such as hydroxyl; resin reinforced siloxanes; and cross linked siloxane polymers.

The rigid silicone polymers useful in the present invention have complex viscosities of at least $2 \times 10^5$ poise (P), preferably about $1 \times 10^7$ poise, where complex viscosity is measured by subjecting a sample to oscillatory shear at a fixed frequency of 0.1 rad/sec at 25° C. using a Rheometric Fluids Spectrometer ® measuring films having a thickness of about 1 millimeter. The resulting viscous and elastic force responses are combined to determine the complex modulus which is divided by the imposed frequency to compute the complex viscosity.

A preferred siloxane gum useful in the present invention is a diphenyl-dimethyl polysiloxane gum having a molecular weight of at least about 500,000, and diphenyl substituted to the extent of 3% or more, preferably at least about 5%.

The siloxane gums may also be filler reinforced to provide additional rigidity. Silica is the preferred filler. Generally such reinforced gums comprise up to about 15-20% silica.

Silicone elastomers useful in the compositions of the present invention are the materials described in U.S. Pat. No. 4,221,688, Johnson et al., issued Sept. 9, 1980, incorporated herein by reference. The actual material described in the patent and what can be put into the present compositions is an aqueous emulsion which dries to form an elastomer upon removal of the water.

The silicone emulsion has a continuous water phase in which there is a dispersed phase which comprises an anionically stabilized hydroxylated polyorganosiloxane, a colloidal silica and a catalyst. The pH of the emulsion should be in the range of from about 9 to about 11.5, preferably from about 10.5 to 11.2. The solids content of the emulsion is generally from about 20% to about 60%, preferably from about 30% to about 50%. The amount of colloidal silica present for each 100 parts by weight of the polydiorganosiloxane is from 1 to 150 parts. On the same basis the amount of a diorganotindicarboxylate (e.g., dioctyl tindilaurate) catalyst is from 0.1 to 2 parts. The elastomer emulsion is used in an amount of from about 0.1% to about 5%, preferably from about 0.5% to about 4%, of the total composition.

Silicon resins useful in the present compositions are silicone polymers with a high degree of crosslinking introduced through the use of trifunctional and tetrafunctional silanes. Typical silanes used in the manufacture of resins are monomethyl, dimethyl, monophenyl, diphenyl, methylphenyl, monovinyl, and methylvinyl chlorosilanes, together with tetrachlorosilane. A preferred resin is one offered by General Electric as GE SR545. This resin is provided as a solution in toluene which is stripped prior to the resin's use.

Other rigid silicone polymers of use herein are those siloxanes which have been sparingly crosslinked but are still soluble in solvents such as cyclomethicone. Precursors for the rigid material can be high molecular weight polydimethyl siloxanes, polydimethyl siloxanes containing vinyl groups and other siloxanes. Methods of crosslinking include heat curing with organic peroxides such as dibenzoyl peroxide and di-t-butyl peroxide, heat vulcanization with sulfur, and high-energy radiation.

Generally, the silicone gum, if used in the present compositions, is dissolved in a volatile carrier, or mixtures thereof, prior to incorporation into the hair care composition. Preferably, the volatile carrier is present in the hair care composition at from about 0.1% to about 20% of the hair care composition. These materials can comprise the volatile liquid hydrocarbon or silicon fluids described supra.

Preferably the rigid silicone polymer and carrier comprises from about 0.1% to about 2.5% of a polydimethylsiloxane gum; from about 0.02% to about 0.7% of fumed silica, and from about 0.4% to about 18% of a volatile silicone carrier.

Alternative hair conditioning materials may be used in the present compositions. Such materials include cationic surfactant materials which are well known as conditioning agents. Preferred cationic surfactants for use as hair conditioning agents in the present compositions are quaternary ammonium-containing cationic surfactant materials. If such a material is included in the present compositions it will be present at levels up to about 2.5%, preferably at from about 0.5% to about 2.0%, by weight of the composition. The preferred quaternary ammonium-containing cationic surfactant for use herein is di(hydrogenated) tallow dimethyl ammonium chloride.

Alternative cationic water-insoluble surfactant hair conditioning agents that may be used in the present compositions are salts of primary, secondary, and tertiary fatty amines. The preferred of these materials is stearamido propyl dimethyl amine. A commercially available material is sold under the trade name Lexamine ® Inolex Company. Preferably, up to about 1% of such materials may be used in the present compositions to provide conditioning benefits.

Hydrolyzed animal protein hair conditioning agents may also be included in the present compositions. Such materials are present in the compositions at levels of from about 0.1% to about 1.5%. An example of a commercially available material is sold under the tradename Crotein Q ® from Croda, Inc.

Fatty alcohols are known hair conditioning agents and may be included in the present compositions. However, as described supra such materials tend to deposit on hair and leave hair feeling dirty after use. Hence, fatty alcohol materials are not included in the compositions of the present invention at levels greater than about 1%.

Combinations of the aforementioned conditioning agents may also be used in the present compositions.

Highly preferred active hair care materials for use with the vehicle systems of the present invention are hair holding/styling polymers. Highly preferred examples of such materials are the silicone-containing copolymers as described in concurrently filed patent applications: Ser. No. 390,559, Torgerson, Bolich and Garbe, filed Aug. 7, 1989; now abandoned, which is the parent application of U.S. Ser. No. 07/505,760 filed Apr. 6, 1990, now abandoned, which is the parent application of U.S. Ser. No. 07/ , filed Aug. 19, 1991; and Ser. No. 390,568, Bolich and Torgerson, filed Aug. 7, 1989; now abandoned, which is the parent application of U.S. Ser. No. 07/505,755, filed Apr. 6, 1990, now abandoned, which is the parent application of U.S. Ser. No. 07/ , filed Aug. 19, 1991; both of which are incorporated by reference herein. Such polymers should have a weight average molecular weight of from about 10,000 to about 1,000,000 and preferably, have a Tg of at least about −20° C. As used herein, the abbreviations "Tg" refers to the glass transition temperature of the non-silicone backbone, and the abbreviation "Tm" refers to the crystalline melting point of the non-silicone backbone, if such a transition exists for a given polymer.

Referred polymer comprise a vinyl polymeric backbone having a Tg or a Tm above about −20° C. and grafted to the backbone, a polydimethylsiloxane macromer having a weight average molecular weight of from about 1,000 to about 50,000, preferably from about 5,000 to about 40,000, most preferably about 20,000. The polymer is such that when it is formulated into the finished hair care composition, when dried, the polymer phase separates into a discontinuous phase which includes the polydimethylsiloxane macromer and a continuous phase which includes the backbone. It is believed that this phase separation property provides a specific orientation of the polymer on hair which results in the desired hair conditioning and setting benefits.

In its broadest aspect, the copolymers utilized in the present application comprise C monomers together with monomers selected from the group consisting of A monomers, B monomers, and mixtures thereof. These copolymers contain at least A or B monomers, together with C monomers, and preferred copolymers contain A, B, and C monomers.

Examples of useful copolymers and how they are made are described in detail in U.S. Pat. No. 4,693,935, Mazurek, issued Sept. 15, 1987, and U.S. Pat. No. 4,728,571, Clemens et al., issued Mar. 1, 1988, both of which are incorporated herein by reference. These copolymers are comprised of monomers A, C, and optionally, B, which are defined as follows. A, when used, is at least one free radically polymerizable vinyl monomer or monomers. B, when used, comprises at least one reinforcing monomer copolymerizable with A and is selected from the group consisting of polar monomers and macromers having a Tg or a Tm above about −20° C. When used, B may be up to about 98%, preferably up to about 80%, more preferably up to about 20%, of the total monomers in the copolymer. Monomer C comprises from about 0.01% to about 50.0% of the total monomers in the copolymer.

Representative examples of A monomers are acrylic or methacrylic acid esters of $C_1$-$C_{18}$ alcohols, such as methanol, ethanol, 1-propanol, 2-propanol, 1-butanol, 2-methyl-1-propanol, 1-pentanol, 2-pentanol, 3-pentanol, 2-methyl-1-butanol, 1-methyl-1-butanol, 3-methyl-1-butanol, 1-methyl-1-pentanol, 2-methyl-1-pentanol, 3-methyl-1-pentanol, t-butanol, cyclohexanol, 2-ethyl-1-butanol, 3-heptanol, benzyl alcohol, 2-octanol, 6-methyl-1-heptanol, 2-ethyl-1-hexanol, 3,5-dimethyl-1-hexanol, 3,5,5-trimethyl-1-hexanol, 1-decanol, 1-dodecanol, 1-hexadecanol, 1-octadecanol, and the like, the alcohols having from about 1–18 carbon atoms with the average number of carbon atoms being from about 4–12; styrene; vinyl acetate; vinyl chloride; vinylidene chloride; acrylonitrile; alpha-methylstyrene; t-butylstyrene; butadiene; cyclohexadiene; ethylene; propylene; vinyl toluene; and mixtures thereof. Preferred A monomers include n-butyl methacrylate, isobutyl methacrylate, 2-ethylhexyl methacrylate, methyl methacrylate, t-butylacrylate, t-butylmethacrylate, and mixtures thereof.

Representative examples of B monomers include acrylic acid, methacrylic acid, N,N-dimethylacrylamide, dimethylaminoethyl methacrylate, quaternized dimethylaminoethyl methacrylate, methacrylonitrile, polystyrene macromer, methacrylamide, maleic anhydride and its half esters, itaconic acid, acrylamide, acrylate alcohols, hydroxyethyl methacrylate, diallyldimethyl ammonium chloride, vinyl pyrrolidone, vinyl ethers (such as methyl vinyl ether), maleimides, vinyl pyridine, vinyl imidazole, other polar vinyl heterocyclics, styrene sulfonate, and mixtures thereof. Preferred B monomers include acrylic acid, N,N-dimethylacrylamide, dimethylaminoethyl methacrylate, quaternized dimethylaminoethyl methacrylate, vinyl pyrrolidone, and mixtures thereof.

The C monomer has the general formula:

wherein X is a vinyl group copolymerizable with the A and B monomers; Y is a divalent linking group; R is a hydrogen, lower alkyl, aryl or alkoxy; Z is a monovalent siloxane polymeric moiety having a number average molecular weight of at least about 500, is essentially unreactive under copolymerization conditions and is pendant from the vinyl polymeric backbone, described above; n is 0 or 1; and m is an integer from 1 to 3. C has a weight average molecular weight of from about 1,000 to about 50,000, preferably from about 5,000 to about 40,000, most preferably from about 10,000 to about 20,000. Preferably, the C monomer has a formula selected from the following group:

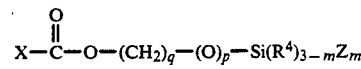

(a preferred monomer, particularly preferred when p = 0 and q = 3)

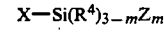

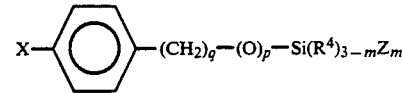

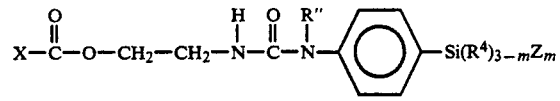

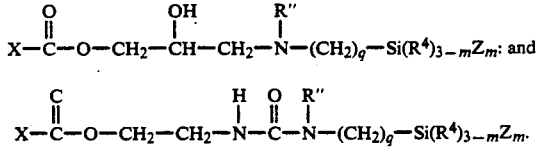

In those structures, m is 1, 2 or 3 (preferably m=1); p is 0 or 1; R" is alkyl or hydrogen; q is an integer from 2 to 6; s is an integer from 0 to 2; X is

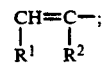

$R^1$ is hydrogen or —COOH (preferably $R^1$ is hydrogen); $R^2$ is hydrogen, methyl or —CH$_2$COOH (preferably $R^2$ is methyl); Z is

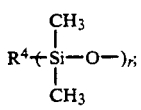

$R^4$ is alkyl, alkoxy, alkylamino, aryl, or hydroxyl (preferably $R^4$ is alkyl); and r is an integer from about 5 to about 700 (preferably r is about 250).

The preferred polymers useful in the present invention generally comprise from 0% to about 98% (preferably from about 5% to about 98%, more preferably from about 50% to about 90%) of monomer A, from 0% to about 98% (preferably from about 7.5% to about 80%) of monomer B, and from about 0.1% to about 50% (preferably from about 0.5% to about 40%, most preferably from about 2% to about 25%) of monomer C. The combination of the A and B monomers preferably comprises from about 50.0% to about 99.9% (more preferably about 60% to about 99%, most preferably from about 75% to about 95%) of the polymer. The composition of any particular copolymer will help determine its formulational properties. For example, polymers which are soluble in an aqueous formulation preferably have the composition: from 0% to about 70% (preferably from about 5% to about 70%) monomer A, from about 30% to about 98% (preferably from about 3% to about 80%) monomer B, and from about 1% to about 40% monomer C. Polymers which are dispersible have the preferred composition: from 0% to about 70% (more preferably from about 5% to about 70%) monomer A, from about 20% to about 80% (more preferably from about 20% to about 60%) monomer B, and from about 1% to about 40% monomer C.

Particularly preferred polymers for use in the present invention include the following (the weight percents below refer to the amount of reactants added in the polymerization reaction, not necessarily the amount in the finished polymer):

acrylic acid/n-butylmethacrylate/polydimethylsiloxane (PDMS) macromer—20,000 molecular weight (10/70/20 w/w/w) (I)

N,N-dimethylacrylamide/isobutyl metahacrylate/PDMS macromer—20,000 molecular weight (20/60/20 w/w/w) (II)

dimethylaminoethyl methacrylate/isobutyl methacrylate/2-ethylhexyl-methacrylate/PDMS macromer—20,000 molecular weight (25/40/15/20 w/w/w/w) (III)

dimethylacrylamide/PDMS macromer—20,000 molecular weight (80/20 w/w) (IV)

t-butylacrylate/t-butylmethacrylate/PDMS macromer—10,000 molecular weight (56/24/20 w/w/w) (V)

b-butylacrylate/PDMS macromer—10,000 molecular weight (80/20 w/w) (VI)

t-butylacrylate/N,N-dimethylacrylamide/PDMS macromer—10,000 molecular weight (70/10/20 w/w/w) (VII)

t-butylacrylate/acrylic acid/PDMS macromer—10,000 molecular weight (75/5/20 w/w/w) (VIII).

The particle size of the copolymer material of the present compositions may have some effect on performance in product. This, of course, will vary from copolymer to copolymer and from product to product.

The copolymer are preferably combined with a solvent for the copolymer prior to combination with the vehicle systems of the present invention.

The solvent selected must be able to dissolve or disperse the particular silicone copolymer being used. The nature and proportion of B monomer in the copolymer largely determines its polarity and solubility characteristics. The silicone copolymers can be designed, by appropriate combination of monomers, for formulation with a wide range of solvents. Suitable solvent for use in the present invention include, but are not limited to, water, lower alcohols (such as ethanol, isopropanol), hydroalcoholic mixtures, hydrocarbons (such as isobutane, hexane, decene, acetone), halogenated hydrocarbons (such as Freon), linalool, hydrocarbon esters (such as ethyl acetate, dibutyl phthalate), volatile silicon derivatives, especially siloxanes (such as phenyl pentamethyl disiloxane, phenethyl pentamethyl disiloxane, methoxypropyl heptamethyl cyclotetrasiloxane, chloropropyl pentamethyl disiloxane, hydroxypropyl pentamethyl disiloxane, octamethyl cyclotetrasiloxane, decamethyl cyclopentasiloxane), and mixtures thereof. Preferred solvents include water, ethanol, volatile silicon derivatives, and mixtures thereof.

The unique vehicle systems of the present invention provide superior performance vis a vis delivery of the active cosmetic component to the hair or skin. This is especially true in the case of hair care compositions. Lower levels of active components may be used in the hair care compositions of the present invention than are used in hair care compositions formulated with alternative thickening systems. These deposition benefits are especially noticeable in the case of silicone hair conditioning agents. The quantity and quality of silicone deposit from the present unique vehicle systems onto hair results in enhanced hair conditioning.

These active cosmetic care materials are generally present at a level of from about 0% to about 20%, preferably from about 0.1% to about 20%, by weight of the cosmetic composition. The 0% level reflects the situation when one of the vehicle components provides the active hair care activity to the present compositions. The level of the active cosmetic care material varies depending upon which active material is chosen, the particular cosmetic composition to be formulated therewith, and the level of benefit desired.

Other optional components that can be added to the cosmetic compositions of the present invention do not provide any direct cosmetic care benefit but instead enhance the composition in some way. Examples of such materials are coloring agents, such as any of the FD&C or D&C dyes; opacifiers; pearlescent aids, such as ethylene glycol distearate or TiO$_2$ coated mica; pH modifiers, such as citric acid, sodium citrate, succinic acid, phosphoric acid, sodium hydroxide, and sodium carbonate; preservatives, such as benzyl alcohol, methyl paraben, propyl paraben, and imidazoldinyl urea; and antioxidants. Such agents generally are used individually at a level of from about 0.001% to about 10%, preferably from about 0.01% to about 5%, of the hair care composition.

The vehicle systems and cosmetic compositions of the present invention can be made using conventional formulation and mixing techniques. Methods of making various types of cosmetic compositions are described more specifically in the following examples.

The following examples illustrate the present invention. It will be appreciated that other modifications of the present invention within the skill of those in the cosmetic composition formulation art can be undertaken without departing from the spirit and scope of this invention.

All parts, percentages, and ratios herein are by weight unless otherwise specified.

EXAMPLE I

The following is a hair styling rinse composition representative of the present invention.

| Component | Weight % |
| --- | --- |
| Styling Agent Premix | |
| Silicone Copolymer[1] | 2.00 |
| Phenylpentamethyl disiloxane | 9.00 |
| Xanthan Premix | |
| Xanthan gum | 0.25 |
| DRO $H_2O$ | 25.00 |
| Main Mix | |
| Dihydrogenated tallow-dimethylammonium chloride (DTDMAC) | 0.50 |
| EDTA, disodium salt | 0.10 |
| D.C. 929[2] | 2.00 |
| Perfume | 0.10 |
| Natrosol Plus CS Grade D-67[3] | 0.75 |
| Locust bean gum | 0.75 |
| Kathon CG[4] | 0.04 |
| DRO $H_2O$ | q.s. to 100% |

[1]20/60/20 N,N-dimethylacrylamide/isobutyl methacrylate/PDMS macromer (20,000 MW), polymer molecular weight about 300,000.
[2]amodimethicone, commercially available from Dow Corning
[3]hydrophobically modified hydroxethylcellulose, having a $C_{16}$ alkyl substitution of from about 0.50% to about 0.95%, by weight, and a hydroxyethyl molar substitution of from about 2.3 to about 3.3, and where the average molecular weight of the hydroxyethyl cellulose prior to substitution is approximately 700,000, available from Aqualon Company.
[4]preservative commercially available from Rohm and Haas The Styling Agent and Xanthan Premixes are blended separately in a conventional manner. The Main Mix is prepared by first heating the DRO (double reverse osmosis) water to 190° F. The DTDMAC, EDTA, and D.C. 929 are then added and the composition is mixed for about 5 minutes. The Natrosol is added with mixing. The locust bean gum is added and the composition is homogenized with a disperser, for example a Gifford-Wood mill, for about 2 minutes. The batch is cooled to 150° F. The xanthan premix, styling agent premix, perfume, and Kathon CG are added and the composition is mixed for about 10 minutes. The batch is then cooled to ambient temperature and stored.

EXAMPLE II

The following is a hair styling rinse composition representative of the present invention.

| Component | Weight % |
| --- | --- |
| Styling Agent Premix | |
| Silicone Copolymer[1] | 3.00 |
| Phenylpentamethyl disiloxane | 9.00 |
| Hydroxypropylpentamethyl disiloxane | 6.00 |
| Silicone Gum Premix | |
| Silicone Gum G.E. SE-76[2] | 0.50 |
| Decamethyl cyclopentasiloxane | 4.00 |
| Main Mix | |
| Natrosol Plus CS Grade D-67[3] | 0.60 |
| Locust bean gum | 0.50 |
| EDTA, disodium salt | 0.15 |
| DTDMAC | 0.65 |
| Glydant[4] | 0.40 |

| Component | Weight % |
| --- | --- |
| DRO $H_2O$ | q.s. to 100% |

[1]10/70/20 acrylic acid/n-butyl methacrylate/silicone macromer, the macromer having a molecular weight of about 20,000, prepared in a manner similar to Example C-2c of U.S. Pat. No. 4,728,571, Clemens, issued March 1, 1988, polymer molecular weight about 300,000
[2]Commercially available from General Electric
[3]hydrophobically-modified hydroxyethyl cellulose commercially available from Aqualon Co.
[4]preservative commercially available from Glyco, Inc.

The composition is prepared as follows. The DRO water is heated to 190° F. The EDTA and DTDMAC are added and mixed for 5 minutes. The Natrosol, locust bean gum and silicone premix are added and dispersed for 2 minutes using a disperser, for example, a Gifford-Wood mill. The batch is cooled to 150° F. and the styling polymer premix and Glydant are added and mixed for 10 minutes. Then the batch is cooled to ambient temperature and stored.

EXAMPLE III

The following is a hair growth promoting composition representative of the present invention.

| Component | Wt. % |
| --- | --- |
| Natrosol Plus CS Grade D-67[1] | 0.75 |
| Locust Bean Gum | 0.75 |
| Minoxidil[2] | 1.00 |
| Preservative/perfume | 0.3 |
| DRO Water | q.s. to 100% |

[1]Hydrophobically-modified hydroxyethyl cellulose commercially available from Aqualon Co.
[2]Hair growth active available from Upjohn The composition is prepared as follows. The DRO water is heated to 190° F. The Locust Bean Gum and Natrosol are added and the composition is homogenized with a disperser, for example a Gifford-Wood mill, for about 5 minutes. The composition is cooled to 120° F. The preservative, perfume and Minoxidil are added and the composition is mixed for about 10 minutes. The composition is then cooled to ambient temperature and stored.

EXAMPLE IV

The following is a hair conditioner composition representative of the present invention.

| Component | Wt. % |
| --- | --- |
| Natrosol Plus Grade 330[1] | 1.25 |
| Xanthan Gum | 0.5 |
| 350 CP PDMS fluid | 0.5 |
| Preservative/perfume | 0.3 |
| DRO Water | q.s. to 100% |

[1]Hydrophobically-modified hydroxyethyl cellulose having a $C_{16}$ alkyl substitution of about 0.4%, by weight, and a hydroxy ethyl molar substitution of from about 3.0 to about 3.7, where the average molecular weight of the hydroxyethyl cellulose prior to substitution is approximately 300,000, commercially available from Aqualon Co.

The composition is prepared as follows. All ingredients are combined and mixed at 60° C. for about 30 minutes.

EXAMPLE V

The following is a hair dye composition representative of the present invention.

| Component | Wt. % |
|---|---|
| Natrosol Plus CS Grade D-67[1] | 1.00 |
| Natrosol 250H[2] | 0.5 |
| Dehyquart SP | 0.10 |
| Preservative/perfume | 0.3 |
| D&C Red 17 | 0.5 |
| Water | q.s. to 100% |

[1]Hydrophobically-modified hydroxyethyl cellulose commercially available from Aqualon Co.
[2]Hydroxyethylcellulose offered by Aqualon Co.

The composition is prepared as follows. All ingredients are combined and mixed at 60° C. for about 30 minutes.

EXAMPLE VI

The following is a hand cream composition representative of the present invention.

| Component | Wt. % |
|---|---|
| Natrosol Plus CS Grade D-67[1] | 1.0 |
| Carboxymethylcellulose | 0.6 |
| EDTA, disodium salt | 0.15 |
| Aloe vera | 0.5 |
| Preservative/perfume | 0.3 |
| Water | q.s. to 100% |

[1]Hydrophobically-modified hydroxyethyl cellulose commercially available from Aqualon Co.

The composition is prepared as follows. All ingredients are combined and mixed at 60° C. for about 30 minutes.

EXAMPLE VII

The following is a hair tonic composition which is representative of the present invention.

| Component | Wt. % |
|---|---|
| Methocel E4M[1] | 0.50 |
| Natrosol Plus CS Grade D-67[2] | 1.50 |
| Dimethicone, 350 CP | 1.00 |
| Kathon CG[3] | 0.03 |
| DRO Water | q.s. to 100% |

[1]Hydroxypropylmethylcellulose offered by Dow Chemical Co.
[2]Hydrophobically-modified hydroxyethyl cellulose commercially available from Aqualon Co.
[3]preservative commercially available from Rohm and Haas The composition is prepared as follows. All ingredients are combined and mixed at 60° C. for about 30 minutes.

EXAMPLE VIII

The following is a hair conditioning rinse which is representative of the present invention.

| Component | Wt. % |
|---|---|
| Xanthan Gum | 0.60 |
| Natrosol Plus CS Grade D-67[1] | 1.60 |
| Silicone Gum Premix | |
| Octamethyl Cyclotetrasiloxane | 3.00 |
| G.E. SE 76[2] | 0.50 |
| Kathon CG[3] | 0.04 |
| DRO Water | q.s. to 100% |

[1]Hydrophobically-modified hydroxyethyl cellulose commercially available from Aqualon Co.
[2]Silicone gum available from General Electric
[3]preservative commercially available from Rohm and Haas The composition is prepared as follows. All ingredients are combined and mixed at 60° C. for about 1 hour.

EXAMPLE IX

The following is an anti-dandruff hair tonic which is representative of the present invention.

| Component | Wt. % |
|---|---|
| Zinc Omadine[1] | 0.05 |
| Natrosol 250M[2] | 0.40 |
| Natrosol Plus CS Grade D-67[3] | 1.25 |
| Dowicil 200[4] | 0.08 |
| DRO Water | q.s. to 100% |

[1]An antidandruff active available from Olin
[2]Hydroxyethyl cellulose commercially available from Aqualon Co.
[3]Hydrophobically-modified hydroxyethyl cellulose commercially available from Aqualon Co.
[4]A preservative available from Dow Chemical Company The composition is prepared as follows. All ingredients are combined and mixed at 60° C. for about 30 minutes.

EXAMPLE X

The following is a hair highlighting rinse which is representative of the present invention.

| Component | Wt. % |
|---|---|
| Polyvinyl Pyrrolidone K 120 | 0.30 |
| Natrosol Plus CS Grade D-67[1] | 1.40 |
| Dihydrogenated Tallow Dimethyl Ammonium Chloride | 0.50 |
| D&C Red #17 | 0.80 |
| Kathon CG[2] | 0.04 |
| DRO Water | q.s. to 100% |

[1]Hydrophobically-modified hydroxyethyl cellulose commercially available from Aqualon Co.
[2]preservative commercially available from Rohm and Haas The composition is prepared as follows. All ingredients are combined and mixed at 60° C. for about 30 minutes.

EXAMPLE XI

The following is a hair styling conditioner which is representative of the present invention.

| Component | Wt. % |
|---|---|
| Natrosol Plus CS Grade D-67[1] | 1.20 |
| Guar Gum | 0.40 |
| Premix | |
| Styling Polymer[2] | 3.00 |
| Phenyl Pentamethyl Disiloxane | 9.00 |
| Adogen 432 CG[3] | 0.50 |
| Kathon CG[4] | 0.04 |
| DRO Water | q.s. to 100% |

[1]Hydrophobically-modified hydroxyethyl cellulose commercially available from Aqualon Co.
[2]A copolymer of isobutylmethacrylate/2-ethylhexylmethacrylate/N,N-dimethyl acrylamide (80/5/15)
[3]Dicetyl dimethyl ammonium chloride available from Sherex
[4]preservative commercially available from Rohm and Haas The composition is prepared as follows. All ingredients are combined and mixed at 60° C. for about 30 minutes.

EXAMPLE XII

The following is a hair styling conditioner which is representative of the present invention.

| Component | Wt. % |
|---|---|
| Disodium EDTA | 0.15 |
| Monosodium Phosphate | 0.04 |
| Disodium Phosphate | 0.12 |
| Dihydrogenated Tallow Dimethyl | 0.75 |

| Component | Wt. % |
|---|---|
| Ammonium Chloride | |
| Locust Bean Gum | 0.70 |
| Natrosol Plus CS Grade D-67[1] | 0.70 |
| Silicone Gum Premix | |
| G.E. SE 76[2] | 0.50 |
| Octamethyl Cyclotetrasiloxane | 3.00 |
| Dextran Purified Crude Grade 2P[3] | 0.25 |
| Styling Polymer Premix | |
| Styling Polymer[4] | 3.00 |
| Phenyl Pentamethyl Disiloxane | 9.00 |
| Hydroxypropyl Pentamethyl Disiloxane | 6.00 |
| Glydant[5] | 0.37 |
| DRO Water | q.s. to 100% |

[1]Hydrophobically-modified hydroxyethyl cellulose commercially available from Aqualon Co.
[2]Silicone Gum available from General Electric
[3]5MM MW Dextran provided by D&O Chemicals
[4]A copolymer of acrylic acid/n-butylmethacrylate/silicone macromer (macromer molecular weight of about 18,000)
[5]preservative commercially available from Rohm and Haas The composition is prepared as follows. All ingredients are combined and mixed at 90° C. for about 1 hour, then cooled to ambient temperature and stored.

EXAMPLE XIII

The following is a styling rinse composition representative of the present invention.

| Component | Weight % |
|---|---|
| Styling Agent | |
| Silicone Copolymer[1] | 3.00 |
| Octamethyl cyclotetrasiloxane | 9.00 |
| Premix | |
| Silicone Gum GE SE 76[2] | 0.50 |
| Decamethyl cyclopentosiloxane | 4.00 |
| Main Mix | |
| Natrosol Plus CS Grade D-67[3] | 1.25 |
| Locust Bean Gum | 0.40 |
| DTDMAC | 0.50 |
| Kathon CG[4] | 0.03 |
| Imidazole | 0.15 |
| Perfume | 0.10 |
| DRO H2O | q.s. to 100% |

[1]80/20 t-butylacrylate/PDMS macromer, the macromer having a molecular weight of about 10,000, prepared in a manner similar to Example C-2b of U.S. Pat. No. 4,728,571, Clemens, issued March 1, 1988
[2]commercially available from General Electric
[3]hydrophobically-modified hydroxyethyl cellulose commercially available from Aqualon Co.
[4]preservative commercially available from Rohm & Haas The composition is prepared as follows. The Styling Agent and Premix are blended separately by conventional means. The Main Mix is prepared by adding all the ingredients and heating to 95° C. for ½ hour with agitation. At the batch is cooled to about 60° C., the Premix and Styling Agent mixes are added to the Main Mix with agitation and the batch is cooled to ambient temperature.

EXAMPLE XIV

The following is a hair styling conditioner representative of the present invention.

| Ingredient | Wt. % |
|---|---|
| Premix: | |
| G.E. SE 76 Gum[1] | 0.80 |
| Cab-O-Sil HS-5[2] | 0.20 |
| Decamethylcyclopentasiloxane | 4.50 |
| Natrosol Plus CS Grade D-67 | 1.40 |
| Locust Bean Gum | 0.58 |
| Adogen 442 - 100P[3] | 0.50 |
| Glydant[4] | 0.37 |
| Disodium EDTA[5] | 0.15 |
| Disodium phosphate | 0.12 |
| Monosodium phosphate | 0.03 |
| P.E.G. 600 | 0.50 |
| DRO H2O | q.s. to 100% |

[1]Polydimethylsiloxane gum offered by General Electric
[2]Fumed silica offered by Cabot Corp.
[3]Dihydrogenated tallow dimethyl ammonium chloride offered by Sherex Chemical Co.
[4]Preservative offered by Glyco, Inc.
[5]Ethylene diamine tetraacetic acid, disodium salt The composition is prepared as follows. The DRO water is first heated to 190° F. The EDTA, monosodium phosphate, and disodium phosphate are added and the composition mixed for about 5 minutes. The silicone premix is then added and the composition mixed. The Natrosol is then added and the composition mixed. The Locust Bean Gum and Adogen 442 are then added and the composition mixed. The composition is then homogenized with a disperser, for example with a Gifford-Wood mill, for about 2 minutes. The batch is cooled to 150° F. The perfume and Glydant are then added and the composition is mixed for about 10 minutes. The composition is then cooled to 80° F. and stored.

EXAMPLE XV

The following is a hair styling conditioner which is representative of the present invention.

| Ingredient | Wt. % |
|---|---|
| Premix 1: | |
| G.E. SE-76 Gum[1] | 0.80 |
| Cab-O-Sil HS-5[2] | 0.20 |
| Decamethylcyclopentasiloxane | 4.50 |
| Premix 2: | |
| G.E. SE-76 Gum | 0.50 |
| Decamethylcyclopentasiloxane | 2.80 |
| Natrosol Plus CS Grade D-67 | 1.39 |
| Locust Bean Gum | 0.56 |
| Adogen 442 - 100P[3] | 0.50 |
| Glydant[4] | 0.37 |
| Disodium phosphate | 0.12 |
| Monosodium phosphate | 0.03 |
| Disodium EDTA[5] | 0.15 |
| DRO H2O | q.s. to 100% |

[1]Polydimethylsiloxane gum offered by General Electric
[2]Fumed silica offered by the Cabot Corp.
[3]Dihydrogenated tallow dimethyl ammonium chloride offered by Sherex Chemical Co.
[4]Preservative offered by Glyco, Inc.
[5]Ethylene diamine tetraacetic acid The composition is prepared as follows. The DRO water is heated to 190° F. The EDTA, monosodium phosphate and disodium phosphate are added and the composition is mixed for about 5 minutes. The silicone premixes are then added to the composition with mixing. The Natrosol is then added to the composition with mixing. The locust bean gum and Adogen 442 are then added to the composition and the composition is homogenized with a disperser, for example with a Gifford-Wood mill for about 2 minutes. The batch is cooled to 150° F. and the perfume and Glydant are added to the composition and the composition is mixed for about 10 minutes. The composition is then cooled to 80° F. and stored.

EXAMPLE XVI

The following is a hair styling condition which is representative of the present invention.

| Ingredient | Wt. % |
| --- | --- |
| Premix: | |
| G.E. SE-76 Gum[1] | 0.10 |
| Decamethylcyclopentasiloxane | 0.60 |
| Natrosol Plus CS Grade D-67 | 1.50 |
| Locust Bean Gum | 0.70 |
| Adogen 442 - 100P[2] | 0.50 |
| Glydant[3] | 0.37 |
| Disodium EDTA[4] | 0.15 |
| Disodium phosphate | 0.12 |
| Monosodium phosphate | 0.03 |
| DRO H$_2$O | q.s. to 100% |

[1] Polydimethylsiloxane gum offered by General Electric
[2] Dihydrogenated tallow dimethyl ammonium chloride offered by Sherex Chemical Co.
[3] Preservative offered by Glyco, Inc.
[4] Ethylene diamine tetraacetic acid The composition is prepared as follows. The DRO water is heated to 190° F. The EDTA, monosodium phosphate and disodium phosphate are added and the composition is mixed for about 5 minutes. The silicone premix is then added to the composition with mixing. The Natrosol is then added to the composition with mixing. The locust bean gum and Adogen 442 are then added to the composition and the composition is homogenized with a disperser, for example with a Gifford-Wood mill for about 2 minutes. The batch is cooled to 150° F. and the perfume and Glydant are added to the composition and the composition is mixed for about 10 minutes. The composition is then cooled to 80° F. and stored.

EXAMPLE XVII

The following is a hair styling rinse composition representative of the present invention.

| Component | Weight % |
| --- | --- |
| Natrosol Plus CS Grade D-67[1] | 0.75 |
| Locust Bean Gum | 0.75 |
| DiTallow DiMethyl Ammonium Chloride (DTDMAC) | 0.75 |
| Citric Acid | 0.07 |
| Sodium Citrate | 0.17 |
| Styling Polymer Premix - | |
| Styling Polymer[2] | 2.5 |
| Phenyl Ethyl Pentamethyl Disiloxane | 1.875 |
| Octamethyl Cyclotetrasiloxane | 5.625 |
| Silicone Gum Premix - | |
| Polydimethyl Siloxane Gum[3] | 0.35 |
| Decamethyl Cyclopentasiloxane | 1.98 |
| Kathon CG | 0.033 |
| Perfume | 0.2 |
| Xanthan Gum[4] | 0.25 |
| DRO Water | q.s. to 100% |

[1] Hydrophobically modified hydroxyethyl cellulose available from Aqualon Corp.
[2] 80/20 t-Butylacrylate/PDMS macromer, the macromer having a molecular weight of about 10,000, prepared in a manner similar to Example C-2b of U.S. Pat. No. 4,728,571, Clemens, issued March 1, 1988
[3] S.E.-76 gum available from General Electric
[4] Readily dispersible xanthan gum The composition is prepared as follows.

The styling polymer premix is prepared by combining the styling polymer, phenyl ethyl pentamethyl disiloxane, and the octamethyl cyclotetrasiloxane.

The silicone gum premix is prepared by combining, in a separate vessel and mixing the silicone gum and the decamethyl cyclopentasiloxane until homogeneous.

About one-half of the DRO water is first heated to about 88° C. The locust bean gum, citric acid, sodium citrate, Natrosol and xanthan gum are added and mixed until homogeneous. The composition is cooled to about 38° C. The styling polymer premix, Kathon CG and perfume are added. The composition is mixed and homogenized with a homogenizer such as a Tekmar homogenizer (preferably in-line).

The remaining DRO water is heated to about 88° C., the DTDMAC is added and mixed until homogeneous. The mixture is then cooled to about 43° C. The silicone gum premix is added and the composition homogenized with a homogenizer (in-line preferred).

The two premixes are then combined and mixed until homogeneous to form the styling rinse composition.

EXAMPLE XVIII

The following is a hair styling rinse composition representative of the present invention.

| Component | Weight % |
| --- | --- |
| Natrosol Plus CS Grade D-67[1] | 0.75 |
| Locust Bean Gum | 0.75 |
| DiTallow DiMethyl Ammonium Chloride (DTDMAC) | 0.75 |
| Stearyl Alcohol | 0.2 |
| Cetyl Alcohol | 0.3 |
| Citric Acid | 0.07 |
| Sodium Citrate | 0.17 |
| Styling Polymer Premix - | |
| Styling Polymer[2] | 2.5 |
| Phenyl Ethyl Pentamethyl Disiloxane | 1.875 |
| Octamethyl Cyclotetrasiloxane | 5.625 |
| Silicone Gum Premix - | |
| Polydimethyl Siloxane Gum[3] | 0.35 |
| Decamethyl Cyclopentasiloxane | 1.98 |
| Kathon CG | 0.033 |
| Perfume | 0.2 |
| Xanthan Gum[4] | 0.25 |
| DRO Water | q.s. to 100% |

[1] Hydrophobically modified hydroxyethyl cellulose available from Aqualon Corp.
[2] 80/20 t-Butylacrylate/PDMS macromer, the macromer having a molecular weight of about 10,000, prepared in a manner similar to Example C-2b of U.S. Pat. No. 4,728,571, Clemens, issued March 1, 1988
[3] S.E.-76 gum available from General Electric
[4] Readily dispersible xanthan gum The composition is prepared as follows.

The styling polymer premix is prepared by combining the styline polymer, phenyl ethyl pentamethyl disiloxane, and the octamethyl cyclotetrasiloxane.

The silicone gum premix is prepared by combining, in a separate vessel and mixing the silicon gum and the decamethyl cyclopenta siloxane until homogeneous.

About one-half of the DRO water is first heated to about 88° C. The locust bean gum, citric acid, sodium citrate, Natrosol and xanthan gum are added and mixed until homogeneous. The composition is cooled to about 38° C. The styling polymer premix, Kathon CG and perfume are added. The composition is mixed and homogenized with a homogenizer such as a Tekmar homogenizer (preferably in-line).

The remaining DRO water is heated to about 88° C., the DTDMAC, stearyl alcohol and cetyl alcohol are added and mixed until homogeneous. The mixture is then cooled to about 43° C. The silicone gum premix is added and the composition homogenized with a homogenizer (in-line preferred).

The two premixes are then combined and mixed until homogeneous to form the styling rinse composition.

EXAMPLE XIX

The following is a hair styling rinse composition representative of the present invention.

| Component | Weight % |
| --- | --- |
| Natrosol Plus CS Grade D-67[1] | 0.75 |
| Locust Bean Gum | 0.75 |
| DiTallow DiMethyl Ammonium Chloride (DTDMAC) | 0.75 |
| Citric Acid | 0.07 |
| Sodium Citrate | 0.17 |
| Styling Polymer Premix - | |
| Styling Polymer[2] | 2.5 |
| Phenyl Ethyl Pentamethyl Disiloxane | 1.875 |
| Octamethyl Cyclotetrasiloxane | 5.625 |
| Silicone Gum/Fluid Premix | |
| Polydimethyl Siloxane Gum[3] | 0.30 |
| 350 centistoke Polydimethyl Siloxane Fluid | 0.20 |
| Kathon CG | 0.033 |
| Perfume | 0.2 |
| Xanthan Gum[4] | 0.25 |
| DRO Water | q.s. to 100% |

[1]Hydrophobically modified hydroxyethyl cellulose available from Aqualon Corp.
[2]80/20 t-Butylacrylate/PDMS macromer, the macromer having a molecular weight of about 10,000, prepared in a manner similar to Example C-2b of U.S. Pat. No. 4,728,571, Clemens, issued March 1, 1988
[3]S.E.-76 gum available from General Electric
[4]Readily dispersible xanthan gum The composition is prepared as follows.

The styling polymer premix is prepared by combining the styline polymer, phenyl ethyl pentamethyl disiloxane, and the ocatamethyl cyclotetrasiloxane.

The silicone gum/fluid premix is prepared by combining in a separate vessel and mixing the silicone gum and silicone fluid until homogeneous.

About one-half of the DRO water is first heated to about 88° C. The locust bean gum, citric acid, sodium citrate, Natrosol and xanthan gum are added and mixed until homogeneous. The composition is cooled to about 38° C. The styling polymer premix, Kathon CG and perfume are added. The composition is mixed and homogenized with a homogenizer such as a Tekmar homogenizer (preferably in-line).

The remaining DRO water is heated to about 88° C., the DTDMAC is added and mixed until homogeneous. The mixture is then cooled to about 43° C. The silicon gum/fluid premix is added and the composition homogenized with a homogenizer (in-line preferred).

The two premixes are then combined and mixed until homogeneous to form the styling rinse composition.

EXAMPLE XX

The following is a hair styling rinse composition representative of the present invention.

| Component | Weight % |
| --- | --- |
| Natrosol Plus - Grade 330 | 1.0 |
| Locust Bean Gum | 0.75 |
| DiTallow DiMethyl Ammonium Chloride (DTDMAC) | 0.75 |
| Citric Acid | 0.07 |
| Sodium Citrate | 0.17 |
| Styling Polymer Premix - | |
| Styling Polymer[2] | 2.5 |
| Phenyl Ethyl Pentamethyl Disiloxane | 1.875 |
| Octamethyl Cyclotetrasiloxane | 5.625 |
| Silicone Gum Premix - | |
| Polydimethyl Siloxane Gum[3] | 0.35 |
| Decamethyl Cyclopentasiloxane | 1.98 |
| Kathon CG | 0.033 |
| Perfume | 0.2 |
| Xanthan Gum[4] | 0.25 |
| DRO Water | q.s. to 100% |

[1]Hydrophobically modified hydroxyethyl cellulose available from Aqualon Corp.
[2]80/20 t-Butylacrylate/PDMS macromer, the macromer having a molecular weight of about 10,000, prepared in a manner similar to Example C-2b of U.S. Pat. No. 4,728,571, Clemens, issued March 1, 1988
[3]S.E.-76 gum available from General Electric
[4]Readily dispersible xanthan gum The composition is prepared as follows.

The styling polymer premix is prepared by combining the styling polymer, phenyl ethyl pentamethyl disiloxane, and the octamethyl cyclotetrasiloxane.

The silicon gum premix is prepared by combining, in a separate vessel and mixing the silicone gum and the decamethyl cyclopenta siloxane until homogeneous.

About one-half of the DRO water is first heated to about 88° C. The locust bean gum, citric acid, sodium citrate, Natrosol and xanthan gum are added and mixed until homogeneous. The composition is cooled to about 38° C. The styling polymer premix, Kathon CG and perfume are added. The composition is mixed and homogenized with a homogenizer such as a Tekmar homogenizer (preferably in-line).

The remaining DRO water is heated to about 88° C., the DTDMAC is added and mixed until homogeneous. The mixture is then cooled to about 43° C. The silicone gum premix is added and the composition homogenized with a homogenizer (in-line preferred).

The two premixes are then combined and mixed until homogeneous to form the styling rinse composition.

EXAMPLE XXI

The following is a hair styling rinse composition representative of the present invention.

| Component | Weight % |
| --- | --- |
| Natrosol Plus CS Grade D-67[1] | 0.75 |
| Locust Bean Gum | 0.75 |
| DiTallow DiMethyl Ammonium Chloride (DTDMAC) | 0.75 |
| Citric Acid | 0.07 |
| Sodium Citrate | 0.17 |
| Styling Polymer Premix - | |
| Styling Polymer[2] | 2.5 |
| Octamethyl Cyclotetrasiloxane | 5.25 |
| Decamethyl Cyclopentasiloxane | 2.25 |
| Silicone Gum Premix - | |
| Polydimethyl Siloxane Gum[3] | 0.35 |
| Decamethyl Cyclopentasiloxane | 1.98 |
| Kathon CG | 0.033 |
| Perfume | 0.2 |
| Xanthan Gum[4] | 0.25 |
| DRO Water | q.s. to 100% |

[1]Hydrophobically modified hydroxyethyl cellulose available from Aqualon Corp.
[2]80/20 t-Butylacrylate/PDMS macromer, the macromer having a molecular weight of about 10,000, prepared in a manner similar to Example C-2b of U.S. Pat. No. 4,728,571, Clemens, issued March 1, 1988
[3]S.E.-76 gum available from General Electric
[4]Readily dispersible xanthan gum The composition is prepared as follows.

The styling polymer premix is prepared by combining the styling polymer, the octamethyl cyclotetrasiloxane, and the decamethyl cyclopentasiloxane.

The silicon gum premix is prepared by combining, in a separate vessel and mixing the silicone gum and the decamethyl cyclopentasiloxane until homogeneous.

About one-half of the DRO water is first heated to about 88° C. The locust bean gum, citric acid, sodium citrate, Natrosol and xanthan gum are added and mixed until homogeneous. The composition is cooled to about 38° C. The styling polymer premix, Kathon CG and perfume are added. The composition is mixed and homogenized with a homogenizer such as a Tekmar homogenizer (preferably in-line).

The remaining DRO water is heated to about 88° C., the DTDMAC is added and mixed until homogeneous. The mixture is then cooled to about 43° C. The silicone gum premix is added and the composition homogenized with a homogenizer (in-line preferred).

The two premixes are then combined and mixed until homogeneous to form the styling rinse composition.

What is claimed is:

1. A cosmetic composition comprising:
   (a) from about 80% to about 100% of a vehicle system which comprises:
      (A) from about 0.3% to about 5.0% by weight of the cosmetic composition of a hydrophobically modified nonionic water-soluble polymer which comprises a water-soluble polymer backbone and hydrophobic groups selected from the group consisting of $C_8$–$C_{22}$ alkyl, aryl alkyl, alkyl aryl groups and mixtures thereof; wherein the ratio of the hydrophilic portion to the hydrophobic portion of the polymer is from about 10:1 to about 1000:1; and
      (B) from about 0.3% to about 5.0% by weight of the cosmetic composition of a water-soluble polymeric thickener having a molecular weight greater than about 20,000; and
      (C) from about 65% to about 99% by weight of the cosmetic composition of a compatible solvent; and
   (b) from 0% to about 20%, by weight, of an active cosmetic component;
wherein said cosmetic compositions comprise no more than about 1.0% of water-soluble surfactants.

2. The composition of claim 1 wherein said hydrophobically modified nonionic water-soluble polymer comprises a nonionic cellulose ether having a sufficient degree of nonionic substitution selected from the group consisting of methyl hydroxyethyl and hydroxypropyl to cause it to be water-soluble and being further substituted with a long chain alkyl radical having 10 to 22 carbon atoms in an amount between about 0.2 weight percent and the amount which renders said cellulose ether less than 1% by weight soluble in water.

3. The composition of claim 2 wherein the vehicle system provides a rheology to the cosmetic composition that is characterized by a shear stress of from 0 to about 50 pascal over a shear rate range of from about 0.04 sec$^{-1}$ to about 25 sec$^{-1}$.

4. The composition of claim 3 wherein the nonionic cellulose ether comprises from about 0.4% to about 3.0% of the cosmetic composition.

5. The composition of claim 4 wherein the nonionic cellulose ether comprises the long-chain radical attached via an ether linkage.

6. The composition of claim 5 wherein the nonionic cellulose ether comprises a water-soluble hydroxypropyl cellulose substituted with a long-chain alkyl radical having 10 to 22 carbon atoms in an amount between about 0.2 weight percent and the amount which renders the hydroxypropyl cellulose less than 1% by weight soluble in water.

7. The composition of claim 6 wherein the nonionic cellulose ether comprises a water-soluble hydroxyethyl cellulose substituted with a long-chain alkyl radical having 10 to 22 carbon atoms in an amount between about 0.2 weight percent and the amount which renders the hydroxyethyl cellulose less than 1% by weight soluble in water.

8. The composition of claim 7 wherein the hydroxyethyl cellulose prior to substitution with the long chain alkyl group has a molecular weight of about 50,000 to 700,000.

9. The composition of claim 8 wherein the water-soluble hydroxyethyl cellulose is substituted with a long chain alkyl radical having about 16 carbon atoms in an amount between about 0.40% to about 0.95%, by weight; the hydroxyethyl molar substitution is from about 2.3 to about 3.7; and the average molecular weight of the unsubstituted cellulose is from about 300,000 to about 700,000.

10. The composition of claim 9 wherein the water-soluble polymeric thickener is selected from the group consisting of hydroxyethyl cellulose, hydroxypropyl cellulose, hydroxypropylmethyl cellulose, polyethylene glycol, polyacrylamide, polyacrylic acid, polyvinyl alcohol, polyvinyl pyrrolidone, dextran carboxymethylcellulose, acacia plant exudate, ghatti plant exudate, tragacanth plant exudate, sodium alginate, propylene glycol alginate, sodium carrageenan, natural polysaccharides, and mixtures thereof.

11. The composition of claim 10 which comprises from about 0.4% to about 3.0% of the water-soluble polymeric thickener.

12. The composition of claim 11 wherein the water-soluble polymeric thickener comprises a natural polysaccharide.

13. The composition of claim 12 wherein the natural polysaccharide is selected from the group consisting of guar gum, locust bean gum, xanthan gum, and mixtures thereof.

14. The composition of claim 3 which additionally comprises from about 0.05% to about 1.0% of a chelating agent.

15. The composition of claim 14 wherein the chelating agent is selected from the group consisting of ethylenediaminetetraacetic acid and salts thereof, nitriloacetic acid and salts thereof, hydroxyethylenediamine triacetic acid and salts thereof, diethylene triamine penta-acetic acid and salts thereof, diethanol glycine and salts thereof, ethanoldiglycine and salts thereof, citric acid and salts thereof, phosphoric acid and salts thereof.

16. The composition of claim 3 wherein from about 0.02% to about 2.5% of the water-soluble polymer is selected from the group consisting of water-soluble polymers having a molecular weight greater than 1,000,000, and water-soluble polymers having strong ionic character.

17. The composition of claim 14 wherein from about 0.05% to about 1.0% of the water soluble polymer is selected from the group consisting of water-soluble polymers having a molecular weight greater than 1,000,000, and water-soluble polymers having strong ionic character.

18. The cosmetic composition of claim 3 which is a hair care composition, wherein said active cosmetic component comprises an active hair care component.

19. The composition of claim 18 wherein the composition comprises no more than about 1% of fatty alcohol materials.

20. The composition of claim 19 wherein the active hair care component is selected from the group consisting of conditioning agents, antidandruff aids, hair growth promoting aids, perfumes, dyes, pigments, sunscreens, hair holding polymers, and mixtures thereof.

21. The composition of claim 20 wherein the active hair care component is selected from the group consisting of a volatile silicone fluid having a viscosity at 25° C. of less than about 10 centipoise, a non-volatile silicone fluid having a viscosity at 25° C. of less than about 100,000 cP, a silicone gum having a viscosity at 25° C. greater than about 1,000,000 cP, and mixtures thereof.

22. The composition of claim 21 wherein the silicone gum is selected from the group consisting of polydimethylsiloxane gums and polyphenylmethylsiloxane gums.

23. The composition of claim 20 wherein the active hair care component comprises from about 0.01% to about 10% of a rigid silicone polymer having a complex viscosity at 25° C. of at least $2 \times 10^5$ poise.

24. The composition of claim 23 which additionally comprises a volatile carrier for the rigid silicone polymer.

25. The composition of claim 24 wherein the rigid silicone polymer is selected from the group consisting of organic substituted siloxane gums, silicone elastomers, filler reinforced polydimethyl siloxane gums, resin reinforced siloxanes and cross-linked siloxane polymers.

26. The composition of claim 25 wherein the volatile carrier is a cyclic silicone containing from about 3 to about 7 silicon atoms.

27. The composition of claim 26 wherein the rigid silicone polymer is a silicone elastomer and the sole volatile carrier is water.

28. The composition of claim 26 wherein the rigid silicone polymer is a filler reinforced polydimethyl siloxane gum.

29. The composition of claim 26 wherein the rigid silicone polymer is an organic substituted siloxane gum.

30. The composition of claim 26 wherein the rigid silicone polymer is a resin reinforced siloxane.

31. The composition of claim 20 wherein the active hair care component comprises from about 0.1% to about 10.0% of a copolymer which has a vinyl polymeric backbone having grafted to its monovalent siloxane polymeric moieties, said copolymer comprising C monomers and components selected from the group consisting of A monomers, B monomers, and mixtures thereof, wherein:
  A is at least one free radically polymerizable vinyl monomer, the amount by weight of A monomer, when used, being up to about 98% by weight of the total weight of all monomers in said copolymer;
  B is at least one reinforcing monomer copolymerizable with A, the amount by weight of B monomer, when used, being up to about 98% of the total weight of all monomers in said copolymer, said B monomer being selected from the group consisting of polar monomers and macromers; and
  C is a polymeric monomer having a molecular weight of from about 1,000 to about 50,000 and the general formula
  $X(Y)_n Si(R)_{3-m}(Z)_m$ wherein
  X is a vinyl group copolymerizable with the A and B monomers
  Y is a divalent linking group
  R is a hydrogen, lower alkyl, aryl or alkoxy
  Z is a monovalent siloxane polymeric moiety having a number average molecular weight of at least about 500, is essentially unreactive under copolymerization conditions, and is pendant from said vinyl polymeric backbone after polymerization
  n is 0 or 1
  m is an integer from 1 to 3
  wherein C comprises from about 0.01% to about 50% of the copolymer.

32. The composition of claim 31 wherein the copolymer comprises from about 5% to about 98% A monomer, from about 0.1% to about 50% C monomer, and from 0% to about 98% B monomer.

33. The composition of claim 20 wherein the active hair care component comprises a lipophilic free radically polymerizable vinyl monomer or a hydrophilic monomer which is copolymerizable with A, or a mixture thereof, and a silicone-containing macromer having a weight average molecular weight of from about 1,000 to about 50,000 based on polydimethylsiloxane selected from the group consisting of $$X-\overset{\overset{O}{\|}}{C}-O-(CH_2)_q-(O)_p-Si(R^4)_{3-m}Z_m$$

$$X-Si(R^4)_{3-m}Z_m$$

$$X-\underset{}{\bigcirc}-(CH_2)_q-(O)_p-Si(R^4)_{3-m}Z_m$$

$$X-\overset{\overset{O}{\|}}{C}-O-CH_2-CH_2-\overset{\overset{H}{|}}{N}-\overset{\overset{O}{\|}}{C}-\overset{\overset{R''}{|}}{N}-\underset{}{\bigcirc}-Si(R^4)_{3-m}Z_m$$

$$X-\overset{\overset{O}{\|}}{C}-O-CH_2-\overset{\overset{OH}{|}}{CH}-CH_2-\overset{\overset{R''}{|}}{N}-(CH_2)_q-Si(R^4)_{3-m}Z_m; \text{ and}$$

$$X-\overset{\overset{C}{\|}}{C}-O-CH_2-CH_2-\overset{\overset{H}{|}}{N}-\overset{\overset{O}{\|}}{C}-\overset{\overset{R''}{|}}{N}-(CH_2)_q-Si(R^4)_{3-m}Z_m;$$

wherein m is 1, 2 or 3; p is 0 or 1; R'' is alkyl or hydrogen; q is an integer from 2 to 6; s in an integer from 0 to 2; X is $$\begin{array}{c} CH=C-; \\ | \quad | \\ R^1 \quad R^2 \end{array}$$

$R^1$ is hydrogen or —COOH; $R^2$ is hydrogen, methyl or —CH$_2$COOH; Z is $$\begin{array}{c} CH_3 \\ | \\ R^4\!-\!(Si-O-)_r \\ | \\ CH_3 \end{array}$$

$R^4$ is alkyl, alkoxy, alkylamino, aryl, or hydroxyl; and r is an integer from about 5 to about 700.

34. The composition of claim 33 wherein monomer A is selected from the group consisting of acrylic acid esters of $C_1$-$C_{18}$ alcohols, methacrylic acid esters of $C_1$-$C_{18}$ alcohols, styrene, vinyl acetate, vinyl chloride, vinylidene chloride, acrylonitrile, alpha-methylstyrene, t-butylstyrene, butadiene, cyclohexadiene, ethylene, propylene, vinyl toluene, polystyrene macromer, and mixtures thereof.

35. The composition of claim 34 wherein monomer B is selected from the group consisting of acrylic acid, methacrylic acid, N,N-dimethylacrylamide, dimethylaminoethyl methacrylate, quaternized dimethylaminoethyl methacrylate, methacrylonitrile, methacryloamide, maleic anhydride, half esters of maleic anhydride, itaconic acid, acrylamide, acrylate alcohols, hydroxyethyl methacrylate, diallyldimethyl ammonium chloride, vinyl pyrrolidone, vinyl ethers, maleimides, vinyl pyridine, vinyl imidazole, styrene sulfonate, and mixtures thereof.

36. The composition of claim 35 wherein monomer A is selected from the group consisting of n-butylmethacrylate, isobutylmethacrylate, 2-ethylhexyl methacrylate, methylmethacrylate, t-butylacrylate, t-butylmethacrylate, and mixtures thereof.

37. The composition of claim 36 wherein monomer B is selected from the group consisting of acrylic acid, N,N-dimethylacrylamide, dimethylaminoethyl methacrylate, quaternized dimethylaminoethyl methacrylate, vinyl pyrrolidone, and mixtures thereof.

38. The composition of claim 37 wherein monomer C has the formula

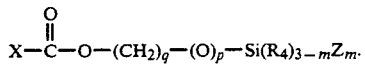

39. The composition of claim 38 wherein $p=0$ and $q=3$.

40. The composition of claim 39 wherein m is 1, r is about 250, $R^4$ is alkyl, $R^1$ is hydrogen, and $R^2$ is methyl.

41. The composition of claim 35 wherein the silicone-containing copolymer is selected from the group consisting of
acrylic acid/n-butylmethacrylate/polydimethylsiloxane macromer—20,000 mw (10/70/20);
N,N-dimethylacrylamide/isobutyl methacrylate/PDMS macromer—20,000 mw (20/60/20);
dimethylaminoethyl methacrylate/isobutyl methacrylate/2-ethylhexyl methacrylate/PDMS—20,000 mw (25/40/15/20);
dimethylaminoethyl methacrylate/isobutyl methacrylate/PDMS—20,000 mw (10/70/20);
quaternized dimethylaminoethyl methacrylate/isobutyl methacrylate/PDMS—20,000 mw (40/40/20);
acrylic acid/methyl methacrylate/PDMS—20,000 mw (40/40/20);
acrylic acid/isopropyl methacrylate/PDMS—20,000 mw (25/65/10);
N,N-dimethylacrylamide/methoxyethyl methacrylate/PDMS—20,000 mw (60/25/15);
dimethylacrylamide/PDMS macromer—20,000 mw (80/20);
t-butylacrylate/t-butyl methacrylate/PDMS macromer—10,000 mw (56/24/20);
t-butylacrylate/PDMS macromer—10,000 mw (80/20);
t-butylacrylate/N,N-dimethylacrylamide/PDMS macromer—10,000 mw (70/10/20);
t-butylacrylate/acrylic acid/PDMS macromer—10,000 mw (75/5/20); and mixtures thereof.

42. A hair care composition comprising:
(a) from about 80% to about 99.9% of a vehicle system which comprises:
(A) from about 0.4% to about 3.0%, by weight of the hair care composition, of a nonionic cellulose ether having a hydroxyethyl molar substitution of from about 2.3 to about 3.7, and being further substituted with a $C_{16}$ alkyl group at from about 0.40% to about 0.95%, by weight, wherein the unsubstituted hydroxyethyl cellulose has an average molecular weight of from about 300,000 to about 700,000;
(B) from about 0.4% to about 3.0%, by weight of the hair care composition, of a water-soluble polymeric thickener having a molecular weight greater than about 20,000 which is selected from the group consisting of locust bean gum and hydroxyethylcellulose having a molecular weight of about 700,000;
(C) from about 0.05% to about 0.3% of a chelating agent which is selected from the group consisting of ethylene diamine tetra acetic acid and salts thereof, citric acid and salts thereof, and phosphoric acid and salts thereof; and
(D) from about 0.05% to about 1.0% of a distributing aid which is selected from the group consisting of xanthan gum and dextran having a molecular weight of greater than 1,000,000; and
(E) from about 65% to about 99%, by weight of the hair care composition, of a compatible solvent; and
(b) from about 0.1% to about 20%, by weight of the hair care composition, of an active hair care component;
wherein said hair care composition comprises no more than about 0.5% of water-soluble surfactants; no more than about 1% of fatty alcohol materials; and
wherein said hair care composition has a rheology that is characterized by a shear stress of from 0 to about 50 pascal over a shear rate range of from about 0.04 sec$^{-1}$ to about 25 sec$^{-1}$.

43. The composition of claim 42 wherein the active hair care component comprises a silicone-containing copolymer selected from the group consisting of
acrylic acid/n-butylmethacrylate/polydimethylsiloxane macromer—20,000 mw (10/70/20);
N,N-dimethylacrylamide/isobutyl methacrylate/PDMS macromer—20,000 mw (20/60/20);
dimethylaminoethyl methacrylate/isobutyl methacrylate/2-ethylhexyl methacrylate/PDMS—20,000 mw (25/40/15/20);
dimethylaminoethyl methacrylate/isobutyl methacrylate/PDMS—20,000 mw (10/70/20);
quaternized dimethylaminoethyl methacrylate/isobutyl methacrylate/PDMS—20,000 mw (40/40/20);
acrylic acid/methyl methacrylate/PDMS—20,000 mw (40/40/20);
acrylic acid/isopropyl methacrylate/PDMS—20,000 mw (25/65/10);
N,N-dimethylacrylamide/methoxyethyl methacrylate/PDMS—20,000 mw (60/25/15);
dimethylacrylamide/PDMS macromer—20,000 mw (80/20);
t-butylacrylate/t-butyl methacrylate/PDMS macromer—10,000 mw (56/24/20);

t-butylacrylate/PDMS macromer—10,000 mw (80/20);
t-butylacrylate/N,N-dimethylacrylamide/PDMS macromer—10,000 mw (70/10/20);
t-butylacrylate/acrylic acid/PDMS macromer—10,000 mw (75/5/20); and mixtures thereof.

44. The composition of claim 42 wherein the active hair care component comprises a silicone conditioning agent which is selected from the group consisting of a conditioning agent comprising, by weight;
 (a) from about 0.1% to about 2.5% of a polydimethylsiloxane gum;
 (b) from about 0.02% to about 0.7% of fumed silica; and
 (c) from about 0.4% to about 18% of a volatile silicone carrier;
a conditioning agent comprising:
 (a) a volatile silicone fluid having a viscosity at 25° C. of less than about 10 centipoise;
 (b) from about 0.5% to about 2.0% of a silicone gum having a viscosity at 25° C. of greater than about 1,000,000 centipoise;
 at ratios of volatile fluid to gum of from about 85:15 to about 50:50; and
a conditioning agent comprising:
 (a) a non-volatile silicone fluid having a viscosity at 25° C. of less than about 100,000 centipoise;
 (b) from about 0.5% to about 2.0% of a silicone gum having a viscosity at 25° C. of greater than 1,000,000 centipoise,
 at ratios of non-volatile fluid to gum of from about 60:40 to about 40:60.

* * * * *